(12) United States Patent
Wahlberg et al.

(10) Patent No.: US 9,364,427 B2
(45) Date of Patent: Jun. 14, 2016

(54) IMPLANTABLE THERAPY SYSTEM FOR TREATING A LIVING BEING WITH AN ACTIVE FACTOR

(75) Inventors: Lars U. Wahlberg, Asnaes (DK); Jens Tornøe, København Ø (DK)

(73) Assignee: NsGene A/S, Ballerup (DK)

( * ) Notice: Subject to any disclaimer, the term of this patent is extended or adjusted under 35 U.S.C. 154(b) by 1519 days.

(21) Appl. No.: 11/920,373

(22) PCT Filed: May 15, 2006

(86) PCT No.: PCT/DK2006/000261
§ 371 (c)(1),
(2), (4) Date: Jan. 23, 2009

(87) PCT Pub. No.: WO2006/122551
PCT Pub. Date: Nov. 23, 2006

(65) Prior Publication Data
US 2009/0227978 A1    Sep. 10, 2009

(30) Foreign Application Priority Data

May 17, 2005 (DK) .................................. 2005 00723
Nov. 25, 2005 (DK) .................................. 2005 01668

(51) Int. Cl.
*A61K 9/00* (2006.01)
*A61M 31/00* (2006.01)

(52) U.S. Cl.
CPC ............ *A61K 9/0024* (2013.01); *A61M 31/002* (2013.01)

(58) Field of Classification Search
CPC ........................... A61K 9/0024; A61M 31/002
USPC ............ 604/27, 36, 522, 57, 264, 273, 890.1, 604/891.1; 206/438, 363, 570, 572; 220/801, 802, 804, 796; 215/316, 341, 215/355, 364
See application file for complete search history.

(56) References Cited

U.S. PATENT DOCUMENTS

| 4,844,242 A | 7/1989 | Chen et al. |
| 4,892,538 A | 1/1990 | Aebischer et al. |

(Continued)

FOREIGN PATENT DOCUMENTS

| JP | H6-210002 | 8/1994 |
| JP | H10-5239 | 1/1998 |

(Continued)

OTHER PUBLICATIONS

International Search Report and Written Opinion for PCT/DK2006/000261 (mail date Jan. 31, 2007),pp. 1-11.

(Continued)

*Primary Examiner* — Theodore Stigell
*Assistant Examiner* — Benjamin Koo
(74) *Attorney, Agent, or Firm* — Kristina Bieker-Brady; Clark & Elbing LLP

(57) ABSTRACT

The invention provides a device for Encapsulated Cell Therapy. The device includes an implantable capsule containing cells which secrete a biologically active compound for providing a biological function. The capsule has a semi permeable outer membrane for delivery of the compound e.g. at a site in the central nervous system or the spinal cord, e.g. in the brain of a patient. The capsule is connected to a tether which e.g. facilitates removal of the capsule from the patient. To facilitate insertion of the capsule into the patient, a stiffener may be attached to the tether to make the tether more rigid. The invention further provides a container for storing a cell therapy device and a method of locating the device in the body of a patient.

23 Claims, 13 Drawing Sheets

(56) References Cited

U.S. PATENT DOCUMENTS

| | | | |
|---|---|---|---|
| 4,968,733 A | | 11/1990 | Müller et al. |
| 4,976,859 A | | 12/1990 | Wechs |
| 5,106,627 A | | 4/1992 | Aebischer et al. |
| 5,156,844 A | | 10/1992 | Aebischer et al. |
| 5,158,881 A | | 10/1992 | Aebischer et al. |
| 5,182,111 A | * | 1/1993 | Aebischer et al. ............ 424/424 |
| 5,283,187 A | | 2/1994 | Aebischer et al. |
| 5,284,761 A | | 2/1994 | Aebischer et al. |
| 5,512,600 A | | 4/1996 | Mikos et al. |
| 5,550,050 A | | 8/1996 | Holland et al. |
| 5,554,148 A | | 9/1996 | Aebischer et al. |
| 5,639,275 A | | 6/1997 | Baetge et al. |
| 5,653,687 A | | 8/1997 | Mills et al. |
| 5,653,975 A | | 8/1997 | Baetge et al. |
| 5,681,740 A | | 10/1997 | Messier et al. |
| 5,725,523 A | | 3/1998 | Mueller |
| 5,773,286 A | | 6/1998 | Dionne et al. |
| 5,786,216 A | | 7/1998 | Dionne et al. |
| 5,795,790 A | | 8/1998 | Schinstine et al. |
| 5,871,487 A | | 2/1999 | Warner et al. |
| 5,874,099 A | | 2/1999 | Dionne et al. |
| 6,123,700 A | * | 9/2000 | Mills et al. ................. 604/890.1 |
| 6,179,826 B1 | * | 1/2001 | Aebischer et al. ............ 604/522 |
| 6,361,771 B1 | | 3/2002 | Tao et al. |
| 6,627,422 B1 | | 9/2003 | Li et al. |
| 2004/0112781 A1 | * | 6/2004 | Hofverberg et al. ........... 206/438 |
| 2006/0258974 A1 | * | 11/2006 | Kennedy, II ..................... 604/22 |

FOREIGN PATENT DOCUMENTS

| | | |
|---|---|---|
| JP | P2000-507854 A | 6/2000 |
| JP | P2003-524621 A | 8/2003 |
| WO | WO 85/02975 | 7/1985 |
| WO | WO 92/19195 | 11/1992 |
| WO | WO 95/05452 | 2/1995 |
| WO | WO 97/34586 | 9/1997 |
| WO | WO 97/44065 | 11/1997 |
| WO | WO 98/05304 | 2/1998 |
| WO | WO 99/52573 | 10/1999 |
| WO | WO 00/60051 | 10/2000 |
| WO | WO 02/28733 | 4/2002 |
| WO | WO2006/122549 | 11/2006 |
| WO | WO2006/122550 | 11/2006 |

OTHER PUBLICATIONS

International Preliminary Report on Patentability (Chapter II) for PCT/DK2006/000261 (completion date Aug. 9, 2007), pp. 1-11.

Buchser et al.; Immunoisolated Xenogeneic Chromaffin Cell Therapy for Chronic Pain: Initianl Clinical Experience (Clinical Investigation), Nov. 1996, Anesthesiology, vol. 85(5) pp. 1005-1012.

Emerich et al.; Alleviation of behavioral deficits in aged rodents following implantation of encapsulated GDNF-producing fibroblasts, Brain Research 736 (1996) 99-110.

Emerich et al.; Implantation of Polymer-Encapsulated Human Nerve Growth Factor-Secreting Fibroblasts Attenuates the Behavioral and Neuropathological Consequences of Quinolinic Acid Injections into Rodent Striatum. Experimental Neurology 130, pp. 141-150 (1994).

Emerich et al.; Implants of Polymer-Encapsulated Human NGF-Secreting Cells in the Nonhuman Primate: Rescue and Sprouting of Degenerating Cholinergic Basal Forebrain Neurons. The Journal of Comparative Neurology 349, pp. 148-164 (1994).

Hoffman et al.; Transplantation of Polymer-Encapsulated Cell Line Genetically Engineered to Release NGF. Experimental Neurology 122, 100-106 (1993).

Kordower et al.; Intrastriatal Implants of Polymer Encapsulated Cells Genetically Modified to Secrete Human Nerve Growth Factor: Trophic Effects upon Cholinergic and Noncholinergic Striatal Neurons. Neuroscience vol. 72, pp. 63-77, 1996.

Kordower et al.; The aged monkey basal forebrain: Rescue and sprouting of axotomized basal forebrain neurons after grafts of encapsulated cells secreting human nerve growth factor. Proc. Natl. Acad. Sci. USA, vol. 91, pp. 10898-10902, Nov. 1994, Neurobiology.

Lindner et al.: Effects of Intraventricular Encapsulated hNGF-Secreting Fibroblast in Aged Rats. Cell Transplantation, vol. 5, No. 2, pp. 205-223 (1996).

Winn et al.; Polymer-encapsulated cells genetically modified to secrete human nerve growth factor promote the survival of axotomized septal cholinergic neurons. Proc. Natl. Acad. Sci. USA, vol. 91, pp. 2324-2328, Mar. 1994, Neurobiology.

Notice of Reasons of Refusal for Japanese Application No. JP 2008-511552, date of dispatch of Jul. 12, 2011, date of draft of Jul. 8, 2011 (3 pages) and English translation thereof (3 pages).

* cited by examiner

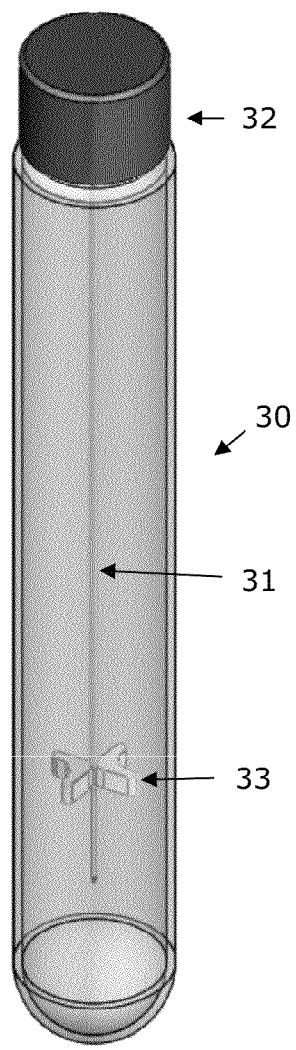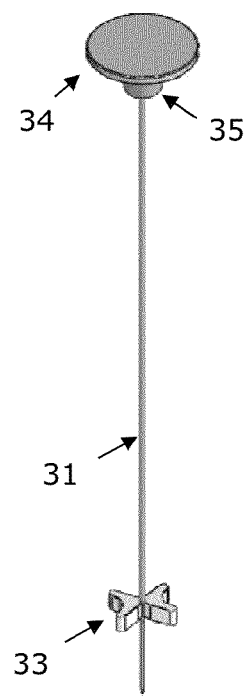
Fig. 5
Fig. 6

IMPLANTABLE THERAPY SYSTEM FOR TREATING A LIVING BEING WITH AN ACTIVE FACTOR

RELATED APPLICATIONS

This application is a national stage application, filed under 35 U.S.C. §371, of International Application No. PCT/DK2006/000261, filed on May 15, 2006 which claims priority to Denmark Patent Application No. PA 2005 00723, filed on May 17, 2005 and Denmark Patent Application No. PA 2005 01668, filed on Nov. 25, 2005.

The invention relates to a system for Encapsulated Cell Therapy, i.e. a device for treating a living being, in the following referred to as the patient, with a biologically active factor. In particular, the invention relates to a device comprising a capsule having a biocompatible outer membrane encapsulating cells which are capable of producing the active factor, the membrane being adapted to allow passage of the active factor. The device further comprises an elongate tether extending in a longitudinal direction from a distal end at which it is joined with the capsule towards an axially opposite proximal end.

BACKGROUND OF THE INVENTION

The technical field of this invention includes the treatment of disorders of the brain and spinal cord, e.g. diseases and disorders which may be remedied by treatment with secretory substances, such as neurotransmitters, conus peptides, neuromodulators, hormones, trophic factors, or growth factors or any compound, which can be produced by and secreted by a cell.

Encapsulated cell therapy is based on the concept of encapsulating cells, which secrete a biologically active factor for local delivery. The technology has the advantages of gene therapy through local and sustained delivery of the biologically active factor synthesised in situ by living cells, combined with retrievability, as the encapsulated cells can be removed again. A further advantage may comprise isolating cells from the recipient host's immune system by using an immunoisolatory capsule. An "immunoisolatory capsule" means that the capsule, upon implantation into a recipient host, minimises the deleterious effects of the host's immune system on the cells in the core of the device and minimises the deleterious effects of the cells in the core of the device on the host. Cells are immunoisolated from the host by enclosing them within implantable polymeric capsules formed by a microporous membrane. This approach prevents the cell-to-cell contact between host cells and implanted cells, reducing or eliminating antigen recognition through direct presentation.

Macroencapsulation involving loading of cells which secrete the active substance into capsules which are delivered through the cannula at the treatment site is an approach to long-term supply of biologically active substances locally e.g. In the brain or spinal cord. A major advantage of macroencapsulation is the retrievability of the capsule and U.S. Pat. No. 6,179,826 and others are concerned with different methods of surgically applying such capsules.

Typically, an insertion site is exposed surgically and a cannula, e.g. provided with an obturator is inserted to define a pathway from the insertion site to a treatment site. At this point the obturator is removed, and a capsule containing cells secreting a biologically active factor is positioned at the treatment site via the passageway. When the capsule is positioned, the cannula is removed. U.S. Pat. No. 6,179,826 discloses that a guidance needle may be inserted into the treatment site, and a guidewire is introduced into the lumen of the needle and is fed through until it enters the treatment site. Once the guidewire is contacting the treatment site, the guidance needle is removed and replaced with a cannula. After retraction of the guidewire, the cannula provides an insertion path for positioning a vehicle containing cells producing the active factors, at the desired site. The guidewire is removed and the vehicle is inserted into the cannula and guided along the pathway of the cannula towards the treatment site. The disclosed vehicle may include a capsule and an integral tether that extends from the capsule and which is of a length sufficient to reach at least from the treatment site to the proximity of the insertion site thereby facilitating fixation of the capsule at the insertion site, e.g. to the outer surface of the skull. The insertion site is subsequently covered by skin. In an alternative approach, the cannula is removed prior to the insertion of the capsule into the treatment site.

To facilitate that the capsule can be pushed into the treatment site by use of the tether, it may be necessary to stiffen the tether, e.g. by locating a small diameter wire portion of the pusher into a hollow cavity of the tether. Until now, the surgical operation, and e.g. the insertion of the wire into the tether is, however, critical and time-consuming, and the wire is only loosely inserted into the tether for subsequent removal when the capsule is in the right position at the treatments site. As the wire is loosely inserted there is also a risk that the wire may penetrate into the core of the device when pressure is applied to one end of the wire to insert the device.

Capsules with or without tethers of the kind known from the prior art have been stored and shipped in storage containers of the kind described in U.S. Pat. No. 5,681,740. The containers have securing means that secure the capsule and/or the tether to the bottom of the container. The securing means serve to avoid undue contact between the capsule and other system components. The securing means have a smaller diameter than the capsule/tether to secure the capsule in position in several places. A certain amount of manipulation is required to remove the capsule from the securing means, as it is fastened in several positions and at the bottom of the container. This may be done by using a forceps or similar surgical instrument. The use of surgical instruments in direct contact with implantable parts of the capsule for retrieval and later handling of the device represents a risk for damaging and contaminating the delicate parts prior to implantation at the treatment site.

DESCRIPTION OF THE INVENTION

It is an object of the invention to facilitate Encapsulated Cell Therapy by providing a device of the kind mentioned in the introduction characterised in that the system further comprises a stiffener which is attached to the tether to make the tether more rigid Since the stiffener is attached to the tether, it is possible to manipulate the tether and the capsule merely by touching the stiffener, and handling of the device is thereby facilitated. As an example, the capsule may be loaded with cells, packed in a sterile package, removed from the package, handled prior to the insertion, and inserted into the treatment site merely by holding the stiffener and the risk of contamination and overloading of the tether and the capsule can be reduced.

The stiffener could be adhesively bonded or mechanically interlocked with the tether, e.g. via surface friction therein between. While the attachment facilitates manipulation of the device merely by touching the stiffener, it may be necessary to remove the stiffener when the capsule is located at the treatment site. For that purpose, the stiffener may be detachable. As an example, the stiffener may be attached by an adhesive which is heat sensitive to allow detachment upon heating the joint between the stiffener and tether. The stiffener could also be fixedly attached to the proximal end of the tether, i.e. opposite the end at which the capsule is attached to the tether. After the insertion of the capsule into the treatment site, that proximal end could be separated from the remaining part of the device, e.g. by cutting the tether into two pieces, and the stiffener may subsequently be removed. Preferably there is a small clearance between the distal end of the stiffener and the capsule to prevent damage to the capsule when pressure is applied to the stiffener. If there is no clearance such damage may occur as the tether may be compressed slightly in a longitudinal direction upon applying pressure to the proximal end of the tether.

When the insertion site has been exposed and a pathway through a cannula has been established, the capsule is positioned at the treatment site via the conduit of the cannula, and the cannula is removed. Since the system comprises an attached stiffener, the capsule is more easily manipulated via the stiffened tether, and during the insertion of the capsule through the conduit, the capsule can be pushed by the stiffened tether without any further preparation thereof. As the stiffener is attached to the tether pressure may be applied to the end of the stiffener without risking damage to the end of the capsule facing the other end of the stiffener.

Upon removal of the stiffener, the rigidity of the therapy system is reduced and the tether is easier to position and fasten, e.g. subcutaneously to the skull. The reduced rigidity of the tether further contributes to a safer implantation and allows the tether to deflect e.g. upon changes in the plasticity of the brain.

Through the increased rigidity of the system the manufacturing steps (filling with cells, sealing after filling, packaging) are also easier performed, and the therapy system can be handled as one integrated system. Furthermore the delicate step of inserting and attaching the stiffener can be carried out prior to sterilisation of the system and prior to filling the capsule with living cells.

The stiffener could be essentially straight and thus further facilitate straightening of the tether during the period of time from the manufacturing of the device until use of the device.

The tether is of a length sufficient to reach from the capsule at the treatment site to a location external to the insertion site and may form an extension of the capsule. To facilitate removal of the capsule from the tissue, e.g. when the treatment comes to an end, or if the capsule must be replaced, the transition between the capsule and the tether could be smooth and without projections of any kind, or the dimension could be increased from the capsule towards the tether. This, obviously, creates an edge between the two parts but since the relatively small capsule forms the distal end of the therapy system, i.e. the end which is towards the body, ancillary damage may be prevented during removal of the capsule. If the capsule and the tether are tubular with circular cross sectional shapes, the radial size of the capsule may therefore preferably be smaller than the radial size of the tether, and the capsule and tether may preferably be joined coaxially to each other.

The tether in many embodiments is adhesively bonded to the membrane part of the capsule. The tether may also have a reduced diameter in the distal end, so that it can be inserted into the membrane part of the capsule. In this case, the tether is preferably also adhesively bonded to an inner surface of the membrane part of the capsule.

The stiffener is provided to make the tether more rigid and resistant towards bending or deflection in a direction transverse to the longitudinal direction. The stiffener thereby facilitates insertion of the capsule into the body. For this purpose, the stiffener could be an elongated member which is attachable to the tether and which is either rigid relative to the tether, or which in combination with the tether, improves the rigidity of the tether. As an example, the stiffener could be made from a material, or with a shape whereby the rigidity is larger than the rigidity of the tether. The stiffener could be made from a rigid metal material and/or made with a circular or with an X-shaped or T-shaped cross sectional shape. As another example, the tether could be relatively rigid against deflection in a first direction transverse to the longitudinal direction, and the stiffener could be relatively rigid against deflection in a second direction transverse to the longitudinal direction whereby the combination of the stiffener and the tether makes the therapy system rigid against deflection in both the first and second direction. The first direction may e.g. be essentially perpendicular to the second direction, and the first and the second direction may e.g. be essentially perpendicular to the longitudinal direction.

In one embodiment, the stiffener comprises a small diameter wire portion which is pushed into an internal conduit of the tether from the proximal end thereof. In this embodiment, the tether may preferably further comprise a large diameter portion wherein the diameter is larger than the diameter of the internal conduit of the tether to prevent this portion from being inserted into the tether. The length of the small diameter portion may preferably be shorter than the length of the tether to prevent complete insertion into the full length of the tether and thereby to ensure a distance between the stiffener and the capsule which is attached to the end of the tether. In this embodiment, the stiffener could be attached to the tether in the proximal end. To attach the stiffener in the proximal end, an outer proximal surface portion of the stiffener could be adhesively bonded to an inner proximal surface portion of the conduit or the outer dimension of the proximal end of the stiffener could match the inner surface of the proximal end of the tether to enable an interference fit between the proximal ends of the stiffener and tether. When the capsule is located at the treatment site, the stiffener could be detached from the inserted part of the device by separating the proximal end of the tether from the distal end of the tether and subsequently sliding the stiffener out of the conduit to increase flexibility of the inserted part of the device. If both the tether and the stiffener are cut straight through the conduit, the stiffener will evidently also be cut into two pieces wherein one of the pieces remains inserted in the distal end of the tether. Since it can be difficult to remove this part of the stiffener from the tether, the tether may preferably be cut in a manner similar to stripping cables, e.g. by a tool substantially corresponding to a cable stripper or simply to use a knife with a blade length which prevents cutting into the stiffener or at least prevents cutting through the stiffener.

In an alternative embodiment, the stiffener comprises a relatively rigid guide tube forming an oblong conduit in which the tether is located.

To attach the stiffener to the tether, the proximal end of the stiffener may have a cross-sectional size, and shape which matches the cross-sectional size and shape of the proximal end of the tether to establish interference fit between contacting surfaces of the two parts. The contacting surfaces of the stiffener and the tether could be prepared with an adhesive compound, or the surfaces could be prepared to have a mutually large surface friction. If the stiffener is located inside the tether, the stiffener may have a proximal end, i.e. an end facing away from the distal insertion end of the system, which proximal end is wider in the cross-sectional direction than the opposite distal end of the stiffener. In this way, contact between an outer surface of the stiffener and an inner surface of the tether may be obtained in the proximal end while a spacing is obtained between an outer surface of the distal end of the stiffener and an inner surface of the distal end of the tether.

In one embodiment, the attachment is provided to release the stiffener from the tether by a pull in the longitudinal direction. If the stiffener is located in a longitudinally extending cavity of a tubular tether, it may be an advantage to provide the stiffener in a length so that it extends further in the longitudinal direction than the tether. In this way, a proximal end of the stiffener remains exposed and allows the user to grip the stiffener and pull it out of the tether.

The exposed proximal end of the stiffener may also be used for handling the therapy system. For this purpose, the proximal end of the stiffener may have structural features to engage with a separate handle, e.g. an ergonomically shaped handle provided for repeated use with different therapy systems. The handle may also be attached to a fixture or a micro drive for use in stereotactic surgery. In one embodiment, the handle is attachable to the stiffener, but not detachable therefrom. After use, the stiffener and the handle can thus be disposed in an assembled state and undesired reuse of the handle is avoided.

The therapy system could be delivered in a container which prevents contamination of the capsule. To facilitate removal of the system from the container, the stiffener and/or the tether may preferably be attached to a closure of the container. In that way, the stiffener may facilitate not only the insertion of the capsule and tether into the patient, but also removal of the system from the container and handing of the system prior to the insertion without touching the insertable parts of the system. Preparatory to the insertion of the system into the patient, the closure could be detached from the stiffener, or the closure could remain attached to the stiffener and be removed from the remaining part of the system when the stiffener is removed from the tether. The container may be a storage device of the kind described in the present application.

To attach the system to the closure, at least one of the tether and/or the stiffener could be adhesively bonded to an inner surface of the closure, or the closure may comprise a protrusion made of a resilient material and provided with a cavity dimensioned to fit closely around the proximal end of the tether and/or the stiffener. In this embodiment, the therapy system could be attached to the closure merely by friction between the cavity and the therapy system.

To further facilitate non-contaminating handling of the system, in particular preparatory to the insertion into the patient, the proximal end of the stiffener and/or the tether may, as previously mentioned, comprise handling means adapted to engage with a separate handle. If the stiffener and/or the tether is attached to the closure of the container, the closure may, however, constitute the handling means and be adapted to be engaged with the handle. For that purpose, an outer surface of the closure may comprise structural features adapted to interlock with cooperating features of the separate handle. In an alternative embodiment, the stiffener and/or the tether, extend(s) through the closure and thereby allow direct contact from outside, e.g. for the purpose of connecting a separate handle prior to the removal of the therapy system from the container.

As a part of the therapy system, the previously mentioned separate handle could be formed from a resilient material and with gripping means to cooperate with corresponding gripping means of the stiffener and/or the tether to enable attachment of the handle to the stiffener and/or to the tether.

The therapy system in addition may comprise a gripping element as described herein.

In a second aspect, the invention provides a storage device of the previously mentioned kind for storing an implantable therapy system. In particular, the storage device may comprise a container with a closure to which the therapy system can be attached.

In a third aspect, the invention provides a method of locating a therapy system of the described kind at a treatment site of a living being.

BRIEF DESCRIPTION OF THE DRAWINGS

In the following, a preferred embodiment of the invention will be described in further details with reference to the drawing in which:

FIG. 5 shows the system located in a container, FIG. 6 shows a closure for the container with the therapy system attached thereto.

DETAILED DESCRIPTION OF THE PREFERRED EMBODIMENTS

Further scope of applicability of the present invention will become apparent from the detailed description given hereinafter. It should be understood that the detailed description and specific examples are given by way of illustration only and various changes and modifications within the spirit and scope of the invention will become apparent to those skilled in the art.

Figure 1A:
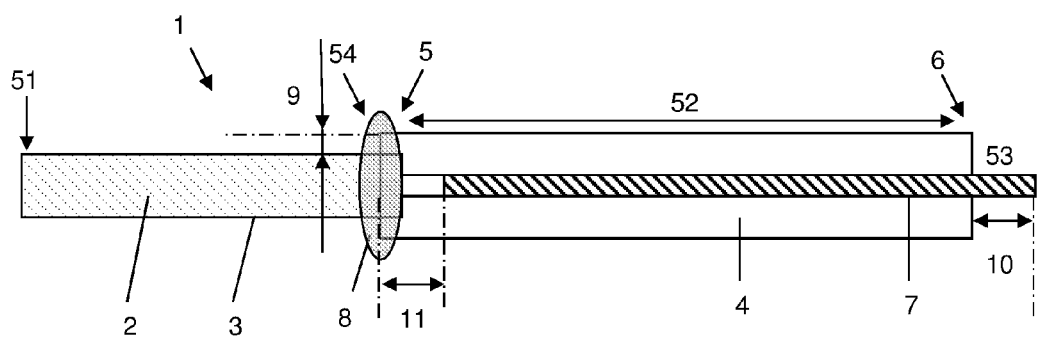
FIGS. 1a-1b illustrate systems according to the invention.
Figure 1B:
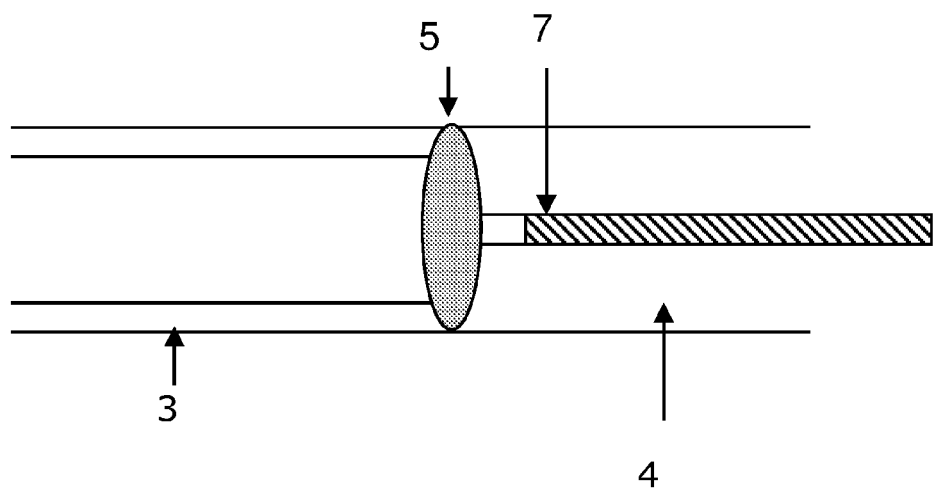

Referring in detail to the drawings, in which identical parts are identically marked, FIG. 1a illustrates an implantable therapy system 1 with a capsule 2 having a biocompatible semi permeable outer membrane 3 encapsulating a cell compartment with living mammalian cells which are capable of producing a compound which provides a biological function. The system further comprises an elongated tether 4 which is joined with the proximal end 54 of the capsule and opposite the distal end 51 of the capsule, and which extends from the distal end 5 of the elongated tether in a longitudinal direction towards an axially opposite proximal end 6 to form a segment 52 of the tether that is non-overlapping with the capsule. The first portion of the stiffener 7 is attached to the tether to make the tether more rigid and thus to facilitate manipulation of the tether and the capsule. The tether and the capsule are joined by glue or by similar fastening means in the area 8. The capsule 1 has a smaller radial size than the tether, indicated by the difference 9, and the second portion of the stiffener 53 extends further in the proximal direction, indicated by the difference 10. The stiffener is, however, not inserted completely into the conduit of the tether and therefore forms a distance 11, i.e., the clearance, to the capsule 3. For example, the capsule may have an outer diameter of 800-1000 μm, and the tether may have an outer diameter of 1000 μm. Thus, the outer diameter of the capsule may be less than the outer diameter of the tether, as shown in FIG. 1a. Additionally. FIG. 1b illustrates a system in which the capsule 3 has an outer diameter of the same size (e.g., 1000 μm) as the outer diameter of the tether 4 (e.g., 1000 μm) with a stiffener 7 located partly inside the tether. The capsule and tether are secured to one another using e.g. glue, at the distal end 5.

Figure 9A:
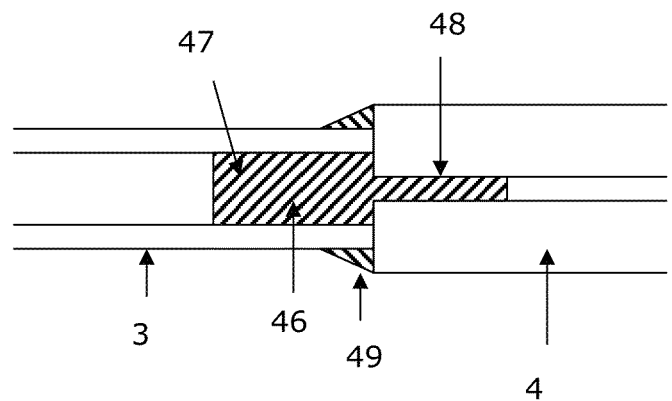
FIG. 9a shows a schematic cross section of a capsule 3 linked to a tether 4 with a rigid linker 46. The linker comprises a first 47 and second 48 part. The edges between the capsule and tether have been smoothed by applying glue 49 to the edge.

FIG. 9a shows an alternative embodiment of fastening means for joining the capsule with the tether. To secure the tether 4 to the capsule 3, a rigid linker 46 may be inserted to link the two parts. A linker may be used when the central cavity of the tether extends all the way to the distal end of said tether. A first part 47 of the linker is adapted to fit inside the semipermeable membrane of the capsule. The fit may be an interference fit, but preferably the linker is secured to the capsule by gluing it. In this respect, the first part of the linker serves as a cell-tight closure of the capsule. A second part 48 of the linker is adapted to fit into a central cavity of the tether and may likewise be secured by simple interference fit or preferably be glued to the tether. The second part of the linker also serves to prevent the stiffener from penetrating into the capsule. For both the first and the second part, the fit should be such that little force is required to insert the linker into the capsule and the tether respectively in order not to damage the delicate parts. The diameters of the first and second part are determined by the inner diameter of the semipermeable membrane part of the capsule and the inner cavity of the tether.

Figure 9B:
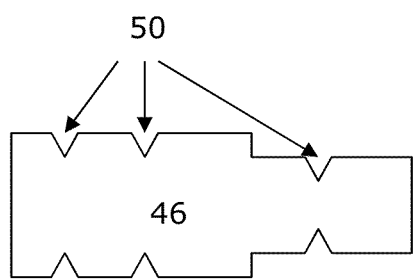
FIG. 9b shows a schematic cross section of an embodiment of a linker 46 with recesses 50 for glue.

To enhance glue attachment to the linker, both the first 47 and the second 48 part may comprise recesses 50 (shown in FIG. 9b) extending around the linker, thereby improving adhesion strength between the linker and tether/membrane. The recesses may be made by milling.

The linker may comprise an optional third central part with an increased diameter relative to the first and the second part. The central part may serve to prevent direct contact between the tether and the capsule.

The linker is made from a rigid material, and may be made from either a rigid polymer such as polysulfone, polyethersulfone, and polycarbonate or from a metal. Metal linkers have the advantage that the capsule can be located easily on an X-ray after implantation. Polymer linkers have the advantage that they do not produce artifacts on MR-scans. In case of metal, a non-magnetic metal is preferred, as patients receiving a capsule are likely to receive MR scanning. Preferred metals include: stainless steel, titanium, gold, silver, platinum, and alloys. The linker may be manufactured by moulding, casting or milling.

In another embodiment, the tether is fastened to the capsule by reducing the diameter of the distal end of the tether and forcing it into the cell compartment of the capsule. Reduction of the diameter may be performed by cutting, milling or thermoforming. Interference fit may suffice to keep the tether in place, and preferably it is further secured by means of glue.

Irrespective of how the capsule and the tether are secured to one another, it should be ensured afterwards that there are no sharp edges between the capsule and tether. Sharp edges may be smoothed during device assembly by glue application 49 (shown in FIG. 9a). Sharp edges may serve as support for growth of the patient's cells after implantation, which may make removal of the device more difficult and cause injury to the patient during removal.

Figure 2:
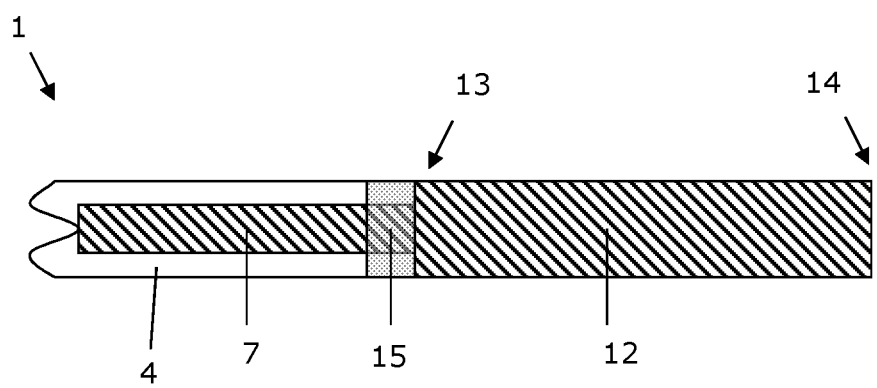
FIG. 2 illustrates details of the proximal end of one embodiment of the system.

FIG. 2 shows details of the proximal end of one embodiment of the system 1. The system comprises, handling means 12 constituted by a handle in one part with the stiffener or constituted by attachment means for attachment of a separate handle to the stiffener. The handling means may form part of the stiffener 7, or the handling means may be connected to the stiffener, e.g. adhesively. The handling means extends axially from its distal end 13, i.e. where the handling means joins with the stiffener towards the axially opposite proximal end 14 of the handling means. A non-flexible part 15, which in a similar manner could form part of the stiffener, may be located between the handle and the stiffener. For removal of the stiffener an instrument, e.g. forceps, can be used to hold the non-flexible part while the attached stiffener is removed from the tether.

Figure 3:
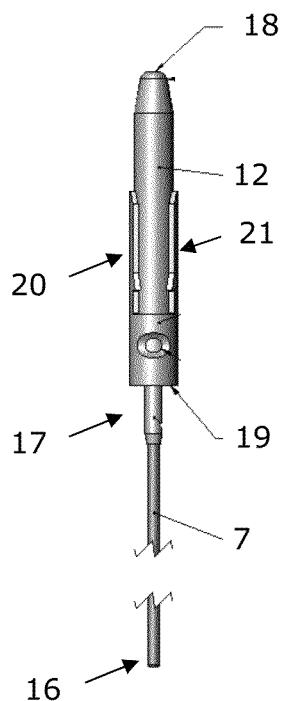
FIG. 3 shows a perspective view of one embodiment of a stiffener for the therapy system.

FIG. 3 shows a perspective view of the stiffener 7 and the handling means 12 shown in further details. The stiffener comprises a distal end 16 and a proximal end 17. The diameter of the proximal end 17 is increased relative to the diameter of the distal end. The increased diameter is provided for the stiffener to fit more tightly into an inner cavity of a tubular tether and thereby to fixate the stiffener to the proximal part of the tether. At the proximal end, the outer surface of the stiffener joins with or forms the handling means 12 that is adapted for attachment with a separate handle and comprises a proximal end 18 and a distal end 19. Guiding fins 20, 21 extend axially and facilitate fixation of the handling means into corresponding slits of a separate handle.

Figure 4:
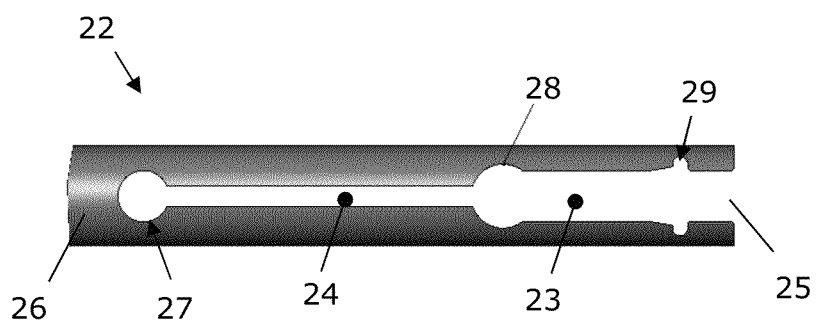
FIG. 4 shows a separate handle adapted for connection with the stiffener shown in FIG. 3.

FIG. 4 shows a separate handle 22 for attachment to the handling means 12 of the stiffener. The handle comprises an elongated cylindrical body with a slit forming a first oblong passage 23 and a second oblong passage 24 being more narrow than the first oblong passage. The slit extends from a distal end 25 of the handle, i.e. the end pointing towards the tether and stiffener, towards an axially opposite proximal end 26 of the handle. Structural features 27, 28, 29 are provided for cooperation with corresponding structural features of the handling means to secure the handle on the handling means and allow transfer of force in a longitudinal direction.

The therapy system is stored and transported inside a storage system. The storage system comprises a storage device and further optional parts. FIG. 5 shows a storage device for storing the therapy system. The storage device comprises a container 30 with an opening into an elongated inner cavity in which the therapy system 31 can be stored in an elongated condition. The opening is closed by a closure 32. The cavity has a wall which is impervious to a fluid storage medium, and during packaging, the therapy system is immersed in the medium in which it is subsequently to be stored and transported until use. The gripping element 33 may be dimensioned relative to the container to protect the capsule from contact with inner wall portions of the container and thereby protects the therapy system. The gripping element is further described with reference to FIG. 7. Generally, the therapy system of the invention is stored in a media storage container which holds a volume of fluid media, a means for securing the system within the media storage container, and a means for sealing the media storage container designed to provide a substantially fluid-tight seal. Preferred embodiments further comprise a media exchange means and a gas exchange means to maintain the viability of the cells in the capsule.

The cap 32 provides a substantially fluid-tight seal when sealingly engaged with the storage container 30. In the preferred embodiment, when the cap is engaged, the storage device is invertible such that the capsule remains submerged in the media and does not come into contact with air bubbles. This ensures that during transportation, if the container is inadvertently inverted, the capsule will not dry out. Preferably, the cap has a seal or liner 34 (e.g., a compressible material such as silicone elastomer) which aids in the formation of a fluid-tight seal.

The liner may be formed by a layered construction approach in which a layer of silicone is placed between two layers of other suitable polymers (e.g., polypropylene or fluoroethylenepropylene). The liner may be fixed to the cap by any suitable means, such as ultrasound welding. Where the liner is formed by layered construction, the inner layer of the liner, that which makes contact with the cap, will be made of the same material as the cap in order to facilitate ultrasound welding. The outer layer may be of any suitable material which will be low friction and sufficiently durable to form a fluid-tight seal. For example, fluorinated perfluoroethylene polypropylene (FEP), a copolymer of hexafluoropropylene and tetrafluoroethylene, is a suitable material for the low-friction layer of the liner. FEP has very similar properties as polytetrafluoroethylene (PTFE), but it is more stable during gamma irradiation sterilization than is PTFE.

A preferred embodiment of the storage and transport apparatus, shown in FIG. 5 further includes gas exchange means and media exchange means.

The ability to exchange gas to the media aids in maintaining the viability of the living cells within the capsule. Alternatively, sufficient oxygen may be introduced into the packaging system by saturating the media prior to engaging the sealing means, or by using a breathable liner.

Gas exchange means may comprise a resealable port which allows for gaseous communication between the outside of a sealed storage container 30 and its interior. The port may be resealed by any suitable method, such as a cap, plug, or preferably self-sealing septum. Such septa are well known in the art.

Media exchange means is similar in design to gas exchange means. For example, media exchange means may also comprise a resealable port for accessing media. Media may be removed from or introduced into storage container 30 using a needle, tube, or other suitable methods.

Exchange of gas and/or medium increases the shelf life of the therapy system of the invention.

The storage system optionally comprises a secondary container which surrounds the container 30. Preferably, the secondary container has means for accessing exchange means of the inner container 30. Additionally, the secondary container may have means for exchanging moisture from the inside of the secondary container to the external atmosphere so as to prevent the excessive buildup of humidity inside the secondary container.

Figure 13A:
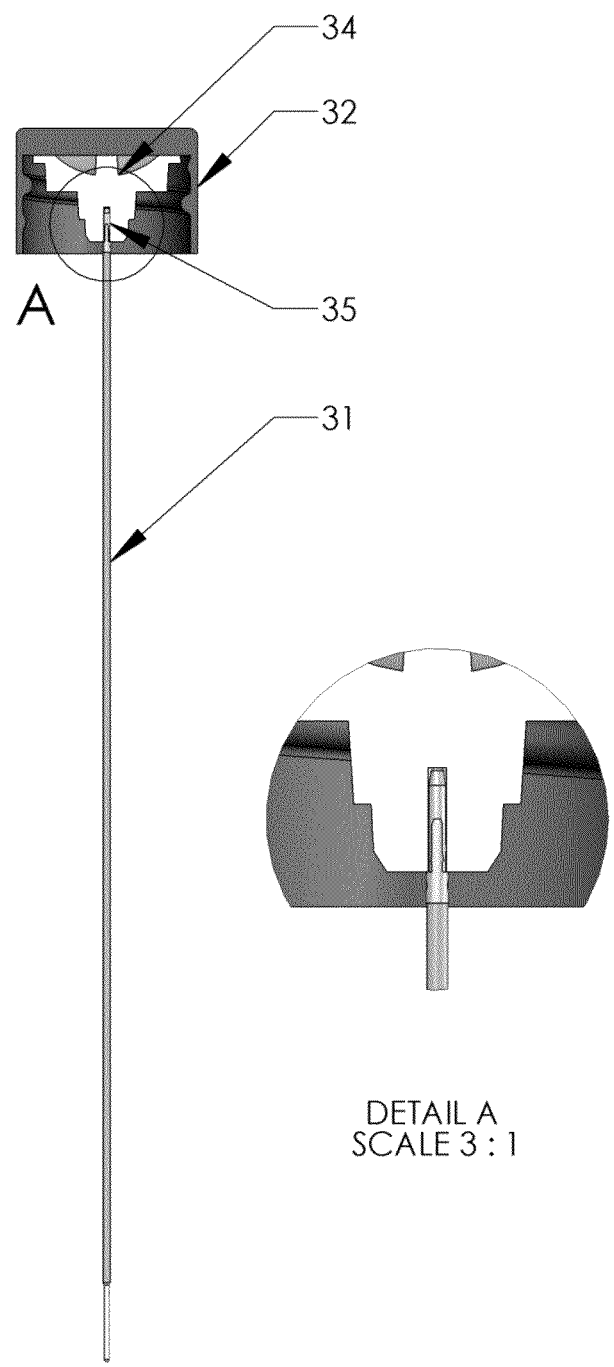
FIG. 13a shows a cross-sectional view (left) of an exemplary embodiment of a closure including a seal and a fixation member with region A (circle) and a magnified view of region A (right) showing the opening of the fixation member dimensioned to fit closely around a portion of the therapy system.
Figure 13B:
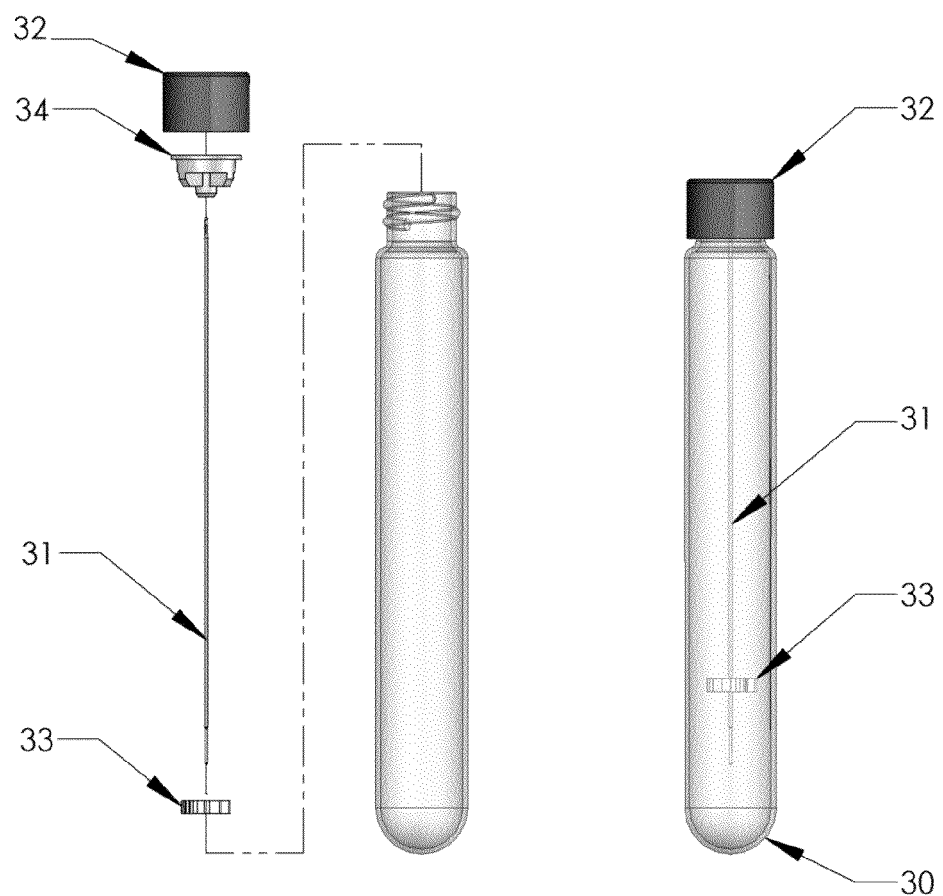
FIG. 13b shows an exploded view (left) of an exemplary embodiment of a closure, a seal, a therapy system, a gripping element, and a container, and a view (right) with the therapy system located in the container.

FIG. 6 shows a view of a seal 34 which may be located in, and attached to the closure 32 to seal the container tightly. The therapy system is detachably attached to the seal. In that way, the user can remove the therapy system from the cavity merely by removing the closure from the container. For attachment of the therapy system to the closure, a fixation member 35 of a resilient material is provided on the inner surface of the seal (i.e., the surface of the seal that faces the inner surface of the container when the closure is closed to seal the container). The fixation member comprises an opening which is dimensioned to narrowly surround a portion of the therapy system and to hold the system by use of the friction between a surface of the fixation member and the outer surface of the therapy system. FIG. 13a (left) shows a cross-sectional view of a therapy system 31 and a closure 32 including a seal 34 and a fixation member 35. FIG. 13a (right) shows an opening in a fixation member 35, where the opening is dimensioned to fit closely around a portion of the therapy system 31 (e.g., at least one of the stiffener and the tether). FIG. 13b shows a closure 32, a seal 34, a therapy system 31, and a gripping element 33 within a container 30.

Figure 7:
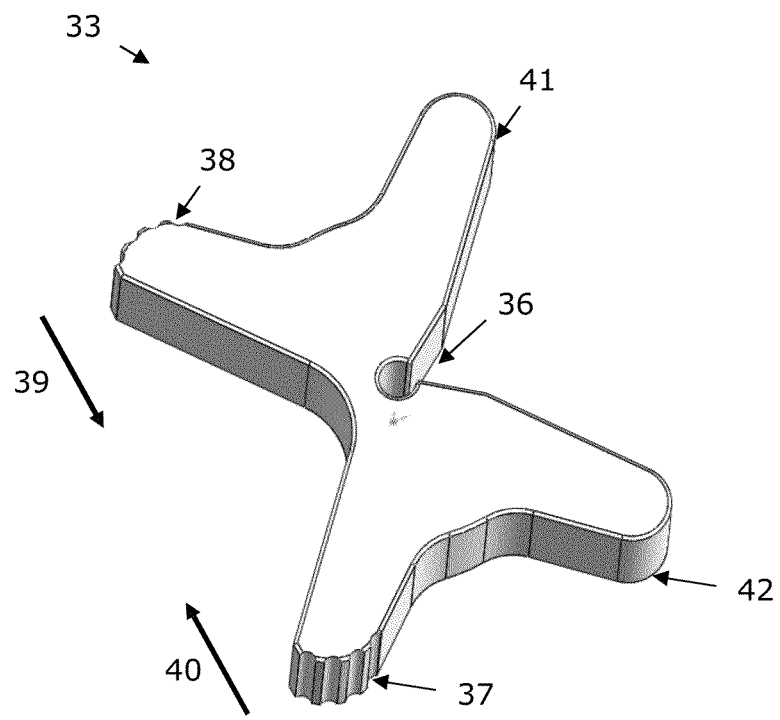
FIG. 7 shows a gripping element to be attached to the tether and/or to the stiffener of the therapy system to facilitate non-contaminating manipulation.

FIG. 7 shows an enlarged view of one embodiment of the gripping element 33 which comprises a passage 36 formed by a semicircular incision between a first arm segment 41 and a second arm segment 42. The passage is shaped and dimensioned so that a surface of the passage is normally in contact with an outer surface of the stiffener and/or the tether to fixate the therapy system to the gripping element. The gripping element is made from a resilient material, and when a user presses the arm segments towards each other, indicated by the arrows 39, 40, the shape and/or the size of the passage changes whereby the grip is released. The disclosed gripping element further comprises third and fourth arm segments 37, 38 which provide distance to an inner surface of the container.

Figure 10:
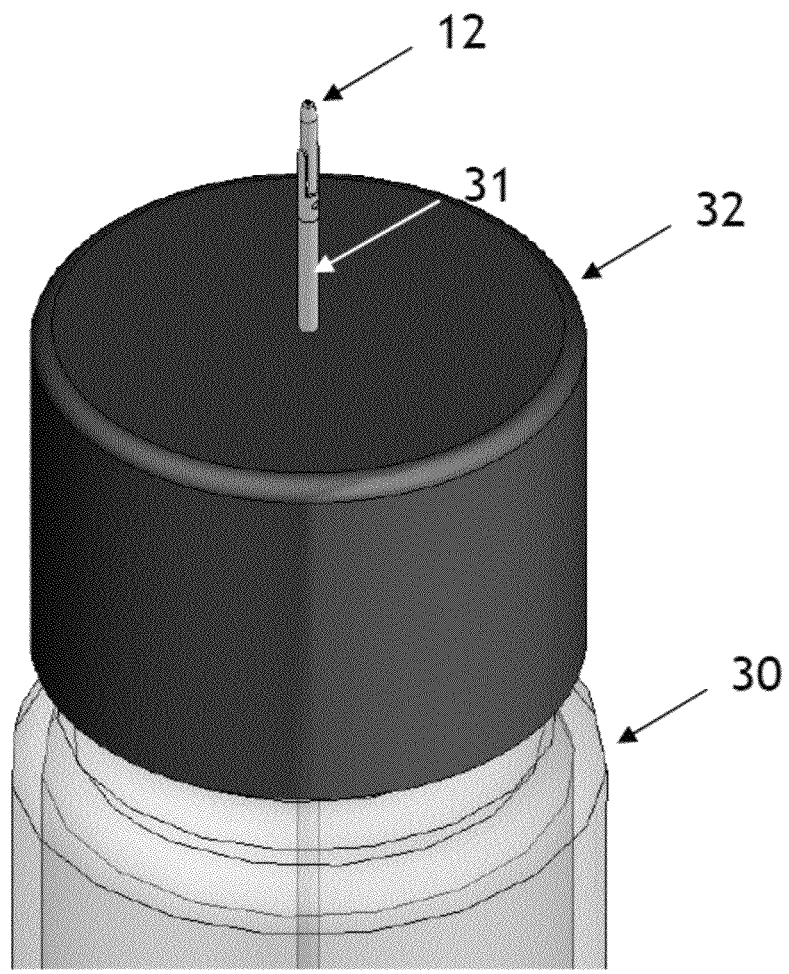
FIG. 10 shows an exposed portion of the therapy system extending through a closure for the container.
Figure 11:
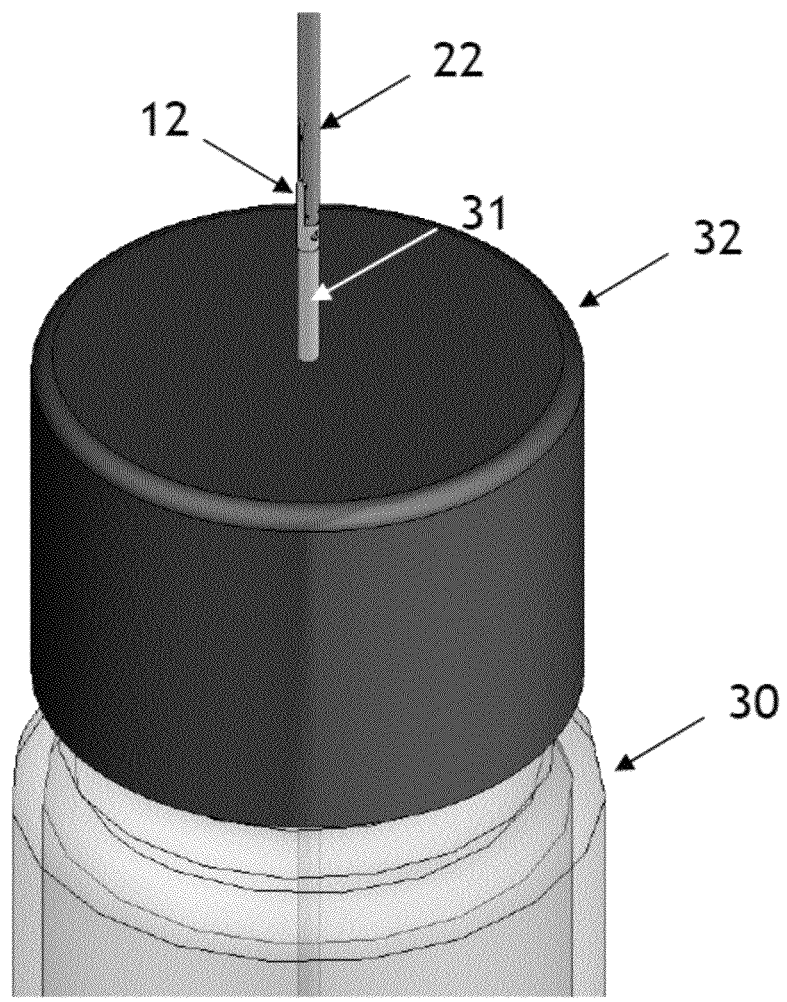
FIG. 11 shows an exposed portion of the therapy system extending through a closure for the container and further including a handling means adapted to engage with a separate handle.
Figure 12A:
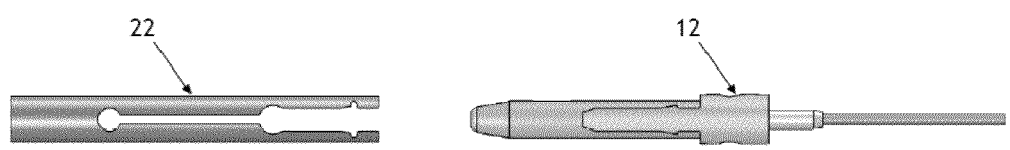
FIG. 12a shows (left) a separate handle for attachment to a handling means and (right) an exemplary system according to the invention.
Figure 12B:
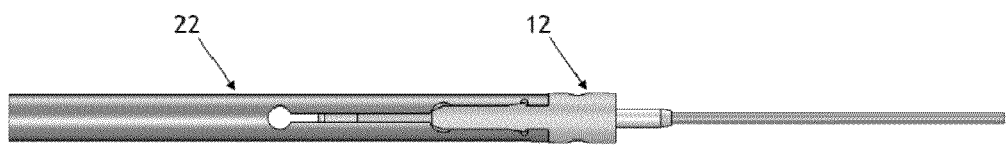
FIG. 12b shows a separate handle attached to a handling means of an exemplary system.

FIG. 10 shows an exposed portion of the therapy system 31. The exposed portion includes at least one of a tether 4 or a stiffener 7, as described in the figures above, of the therapy system 31. In addition, the exposed portion extends through a closure 32 and is located outside the container 30. FIG. 11 shows the therapy system of FIG. 10 including a separate handle 22. The exposed portion includes at least one of a tether 4 or a stiffener 7, as described in the figures above, of the therapy system 31 and extends through the closure 32. In addition, the exposed portion includes a handling means 12 adapted to engage with a separate handle 22. FIG. 12a shows a separate handle 22 for attachment to a handling means and a system according to the invention having a handling means 12 adapted to engage with a separate handle. An exemplary separate handle 22 and its structural components are shown in FIG. 4. FIG. 12b shows the separate handle 22 attached to a handling means 12 of a system.

Gripping Element

In one embodiment the implantable therapy system a gripping element detachably attached to the tether.

The detachably attached gripping element provides several advantages over the prior art therapy systems devoid of such gripping elements. The gripping element provides a "handle" for use during handling of the delicate therapy system, whereby direct contact with the parts of the therapy system that come into contact with tissue after implantation (the capsule and tether) is avoided. The gripping element may be used for gripping when the therapy system is filled with cells and serves as a convenient handle for the surgeon to insert the therapy system into a trocar or cannula for implantation or to secure the therapy system to a stereotactic. As the gripping element is detachable, the surgeon can easily remove the gripping element from the tether before the therapy system is finally inserted into the brain or another body part. Finally the gripping element serves to protect the capsule part of the therapy system from contact with inner walls of a storage container during transport and storage because it ensures a minimum distance to said walls.

A gripping element may be detachably attached to the tether and/or the stiffener to allow a medical practitioner to manipulate the therapy system without direct contact with insertable parts of the stiffener and/or the tether. The gripping element may form a passage with an inner surface which closely surrounds, or at least partly surrounds an outer surface of the tether and/or the stiffener and which in a relaxed state is in contact therewith to fixate the tether and/or the stiffener in the passage. The gripping element could be made from a resilient material which is shaped so that the shape and/or the size of the passage can be changed by a releasing deflection of the gripping element to release the fixation of the tether and/or the stiffener in the passage. The releasing deflection could be obtained by squeezing the gripping element by finger pressure, and it could be supported by the provision of first and a second arm segments extending in different directions away from the passage. In one embodiment, the passage forms the shape of a semicircular incision between the first and second arm segment. The arms preferably have sufficient size and thereby strength to transmit the force applied to them to the center of the gripping element causing opening of the passage and not just deformation of the arms.

In a preferred embodiment, the gripping element forms a passage with a cross sectional shape and size, the gripping element being changeable between a relaxed state wherein an inner surface of the passage contacts an outer surface of the tether to attach the gripping element to the therapy system and a strained state wherein the passage is deflected to release the therapy system from the gripping element.

The gripping element may be shifted between the relaxed and the strained state by application of a force to an outer surface of the gripping element. The force may be a releasing pressure to an outer surface of the gripping element. To facilitate application of the releasing pressure the gripping element may further comprise a first and a second arm segment extending from the passage in different directions.

The above-mentioned passage in one embodiment forms the shape of a semicircular incision between the first and second arm segment. The gripping element may comprise as many arm segments as desired. Thus it may comprise at least a third arm segment, such as at least a fourth arm segment, for example at least a fifth arm segment, such as at least a sixth arm segment. It is preferred that the gripping element comprises at least four arm segments to facilitate handling of the therapy system and to ensure that it can be kept away from the inner surfaces of a storage container.

The gripping element preferably remains attached to the tether during filling with cells, culture, storage, and transport. This may be obtained by selecting materials for the tether and gripping element that have a high sliding friction. In a particularly preferred embodiment, the gripping element thereby does not move along the longitudinal axis of the tether.

For ease of manipulation the gripping element is detachable using force applied by fingers and optionally forceps or other non-powered surgical equipment. In this way the surgeon or a nurse can easily remove the gripping element.

The gripping element may in some embodiments be detachably attached to the tether and/or stiffener. As the stiffener preferably is located inside the tether, the gripping element thus can be said to be attached to both. However it is conceivable that the gripping element is only attached to the stiffener.

The gripping element may be made from any material suitable for the purpose, taking due consideration to the fact that the gripping element is not intended for implantation but may be in contact with the growth/storage medium that is also in contact with encapsulated cells. In a preferred embodiment, the gripping element comprises a resilient material. The use of a resilient material protects the tether and may also assist in making the gripping element changeable between a strained and a released state. The gripping element may also include a further rigid material. It may be advantageous to manufacture the arms of a rigid material to ensure better transfer of force and/or to make the surface of the arms non-slippery in wet condition.

The resilient material may include silicone or other flexible, biocompatible polymer with high sliding friction at interference fit.

The gripping element may be kept in position on the tether and/or stiffener by an interference fit, or be mechanically interlocked with the tether and/or the stiffener, e.g. via surface friction therein between the gripping element and the tether and/or the stiffener.

In one embodiment the therapy system is contained in a container of the kind described in the present application which prevents contamination of the capsule. To this end, the gripping element is preferably dimensioned relative to the container to prevent contact between the capsule part of the system and inner walls of the container.

In a further embodiment the biocompatible semi-permeable outer membrane encapsulates cells capable of secreting a biologically active compound. When the capsule comprises cells, it needs to be kept in a growth/storage medium in a container to maintain viability of the cells until implantation.

The exact choice of dimensions for the gripping element part of the system depends on the dimensions of the therapy system itself, in particular on the dimensions of the tether and the storage container in which the system is to be stored and shipped prior to implantation. Therefore the following dimensions are meant to be merely guiding and not of any limiting nature.

The gripping element typically may extend from 2 to 50 mm in a direction perpendicular to the axis of the tether. Preferably, the distance is less than 40 mm, more preferably less than 30 mm, such as 20 mm or 10 mm. The smaller this distance, the smaller a container is needed for storage. A certain minimum size is required to keep the capsule part of the therapy system from touching the walls of the container. This minimum distance depends on the length of the therapy system and its flexibility.

The diameter or cross section of the passage having an inner surface which essentially surrounds or at least partly surrounds the tether and/or the stiffener is preferably equal to or slightly smaller than the diameter of the tether/stiffener. When a slightly smaller diameter of the passage is used, the gripping element is kept in position by the pressure force applied to the tether/stiffener. In some embodiments, the passage has a diameter at least 5% smaller than the diameter of the tether, preferably at least 10%, such as at least 15%, for example at least 20%.

The gripping element may comprise at least one symmetry plane through the longitudinal axis of the tether/stiffener. However, it may be advantageous to use an essentially non-symmetric gripping element. One larger part of the gripping element may thus serve as a handle that is easy to grip for the surgeon or the manufacturer, while a second smaller part of the gripping element serves to provide the desired distance to the inner walls of a storage container.

The thickness of the gripping element typically may be from 0.5 to 20 mm, preferably from 0.5 to 10 mm, more preferably from 1.5 mm.

In dimensioning the size of the gripping element due consideration should be taken to the size of the container. Thus the clearance between the container and the gripping element may be at least 0.2 mm, preferably at least 0.5 mm. Due consideration should be taken to the dimensions of the opening of the container, which may be of a smaller size than the body of the container.

Storage Container

In another embodiment the therapy system is stored in a storage device comprising a container with an opening into a cavity for storage of the system immersed in a fluid medium, and a closure for closing the opening, characterised in that the closure comprises fixation means for attaching the therapy system to the closure.

The container may form an elongated cavity extending in a longitudinal direction for storage of an elongated system in an outstretched condition. Other inner shapes of the container are conceivable depending on the dimensions of the therapy system.

The closure may comprise a fixation member of a resilient material and provided with an opening dimensioned to narrowly surround a gripped portion of the system thereby to detachably attach the system to the closure. Preferably, the fixation member forms part of a seal provided between the container and the closure to facilitate antibacterial storage of the implantable therapy system. Additionally, the closure may comprise an outer surface with fixation means for attaching a separate handle to the closure.

Encapsulated Cell Therapy

The cell capsule, in the following referred to as the capsule has a membrane which is tailored to control diffusion of molecules, such as growth factor hormones, neurotransmitters, peptides, antibodies and complements, based on their molecular weight or size. Using encapsulation techniques, cells can be transplanted into a host without immune rejection, either with or without use of immunosuppressive drugs. Useful biocompatible polymer capsules usually contain a core that contains cells, either suspended in a liquid medium or immobilised within an immobilising matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue and allows nutrients to diffuse easily into the capsule and support the encapsulated cells. The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the recombinant cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, or biocompatible metals. Also, bonded fibre structures can be used for cell implantation (U.S. Pat. No. 5,512,600, incorporated by reference). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (WO 98/05304, incorporated by reference). Woven mesh tubes have been used as vascular grafts (WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

The jacket preferably has a molecular weight cutoff of less than 1000 kD, more preferably between 50-700 kD, more preferably between 70-300 kD, more preferably between 70-150 kD, such as between 70 and 130 kD. The molecular weight cutoff should be selected to ensure that the bioactive molecule can escape from the capsule while protecting the encapsulated cells from the immune system of the patient.

The thickness of the jacket typically lies in the range of 2 to 200 microns, more preferably from 50 to 150 microns. The jacket should have a thickness to give the capsule sufficient strength to keep the cells encapsulated and should with this in mind be kept as thin as possible to take up as little space as possible.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fibre membrane. Such membranes, and methods of making them are disclosed by U.S. Pat. Nos. 5,284,761 and 5,158,881, incorporated by reference. The surrounding semipermeable membrane may be formed from a polyether sulfone hollow fibre, such as those described by U.S. Pat. No. 4,976,859 or U.S. Pat. No. 4,968,733, incorporated by reference. An alternate surrounding semipermeable membrane material is poly (acrylonitrile/covinyl chloride) (Pan-PVC).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations, which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. A particularly preferred shape is cylinder-shaped as such a shape is easily produced from hollow fibres which can be produced industrially.

When macrocapsules are used, preferably at least $10^3$ cells are encapsulated, such as between $10^3$ and $10^8$ cells are encapsulated, most preferably $10^5$ to $10^7$ cells are encapsulated in each device. Of course, the number of cells in each capsule depends on the size of the capsule. As a rule of thumb, in a capsule with foam (described below) the present inventors have found that loading between 10,000 and 100,000 cells per µL of capsule (volume calculated as the internal volume including foam), more preferably from 25,000 to 50,000 cells per µL, more preferably from 30,000 to 40,000 cells per µL. The number of cells to be loaded also depends on the size of the cells.

Dosage may be controlled by varying the dimensions (length, diameter) of the capsule and/or by implanting a fewer or greater number of capsules, preferably between 1 and 10 capsules per patient.

A macrocapsule in the present context is a capsule having a volume of at least 1 µL, such as from 1 to 10 µL.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see WO 97/34586, incorporated by reference).

Foam Scaffolds:

The foam scaffold may be formed from any suitable material that forms a biocompatible foam with an open cell or macroporous structure with a network of pores. An open-cell foam is a reticulate structure of interconnected pores. The foam scaffold provides a non-biodegradable, stable scaffold material that allows attachment of adherent cells. Among the polymers that are useful in forming the foam scaffolds for the devices of this invention are thermoplastics and thermoplastic elastomers.

Some examples of thermoplastic materials useful in forming suitable foam scaffolds are: acrylic, modacrylic, polyamide, polycarbonate, polyester, polyethylene, polypropylene, polystyrene, polysulfone, polyethersulfone and polyvinylidene fluoride. Some examples of elastomer materials useful in forming suitable foam scaffolds are: polyamide polyester, polyethylene, polypropylene, polystyrene, polyurethane, polyvinyl alcohol, polyethylene vinylacetate, and silicone.

Thermoplastic foam scaffolds made from polysulfone and polyethersulfone, and thermoplastic elastomer foam scaffolds made from polyurethane and polyvinyl alcohol are preferred.

The foam must have some (but not necessarily all) pores of a size that permits cells to attach to the walls or surfaces within the pores. The pore size, pore density and void volume of the foam scaffold may vary. The pore shape may be circular, elliptical or irregular. Because the pore shape can vary considerably, its dimensions may vary according to the axis being measured. For the purposes of this invention, at least some pores in the foam should have a pore diameter of between 20-500 µm, preferably between 50-150 µm. Preferably the foregoing dimensions represent the mean pore size of the foam. If non-circular, the pore may have variable dimensions, so long as its size is sufficient to permit adherent cells to attach to the walls or surfaces within the pore. In one embodiment, foams are contemplated having some elliptical pores that have a diameter of 20-500 µm along the minor axis and a diameter of up to 1500 µm along the major axis.

In addition to the foregoing cell permissive pores sizes, preferably a least a fraction of the pores in the foam should be less than 10 µm to be cell impermissive but still provide channels for transport of nutrients and biologically active molecules throughout the foam.

Pore density of the foam (i.e., the number per volume of pores that can accommodate cells, as described above) can vary between 20-90%, preferably between 50-70%.

Similarly, the void volume of the foam may vary between 20-90%, preferably between 30-70%.

The walls or surfaces of the pores may be coated with an extracellular matrix molecule or molecules, or other suitable molecule. This coating can be used to facilitate adherence of the cells to the walls of the pores, to hold cells in a particular phenotype and/or to induce cellular differentiation.

Preferred examples of extracellular matrix molecules (ECM) that can be adhered to the surfaces within the pores of the foams include: collagen, laminin, vitronectin, polyornithine and fibronectin. Other suitable ECM molecules include glycosaminoglycans and proteoglycans; such as chrondroitin sulfate, heparin sulfate, hyaluron, dermatan sulfate, keratin sulfate, heparan sulfate proteoglycan (HSPG) and elastin.

The ECM may be obtained by culturing cells known to deposit ECM, including cells of mesenchymal or astrocyte origin. Schwann cells can be induced to synthesize ECM when treated with ascorbate and cAMP. See, e.g., Baron-Van Evercooren et al., "Schwann Cell Differentiation in vitro: Extracellular Matrix Deposition and Interaction," Dev. Neurosci., 8, pp. 182-96 (1986).

In addition, adhesion peptide fragments, e.g., RGD containing sequences (ArgGlyAsp), YIGSR-containing sequences (TyrIleGlySerArg), as well as IKVAV containing sequences (IleLysValAlaVal), have been found to be useful in promoting cellular attachment. Some RGD-containing molecules are commercially available—e.g., PepTite-2000™ (Tellos).

The foam scaffolds of this invention may also be treated with other materials that enhance cellular distribution within the device. For example, the pores of the foam may be filled with a non-permissive hydrogel that inhibits cell proliferation or migration. Such modification can improve attachment of adherent cells to the foam scaffold. Suitable hydrogels include anionic hydrogels (e.g., alginate or carageenan) that may repel cells due to charge. Alternately, "solid" hydrogels (e.g., agarose or polyethylene oxide) may also be used to inhibit cell proliferation by discouraging binding of extracellular matrix molecules secreted by the cells.

Treatment of the foam scaffold with regions of a non-permissive material allows encapsulation of two or more distinct cell populations within the device without having one population overgrow the other. Thus non-permissive materials may be used within the foam scaffold to segregate separate populations of encapsulated cells. The distinct populations of cells may be the same or different cell types, and may produce the same or different biologically active molecules. In one embodiment, one cell population produces a substance that augments the growth and/or survival of the other cell population. In another embodiment, multiple cell types producing multiple biologically active molecules are encapsulated. This provides the recipient with a mixture or "cocktail" of therapeutic substances.

The devices of this invention may be formed according to any suitable method. In one embodiment, the foam scaffold may be pre-formed and inserted into a pre-fabricated jacket, e.g., a hollow fibre membrane, as a discrete component.

Any suitable thermoplastic or thermoplastic elastomer foam scaffold material may be preformed for insertion into a pre-fabricated jacket. In one embodiment we prefer polyvinyl alcohol (PVA) sponges for use as the foam scaffold. Several PVA sponges are commercially available. For example, PVA foam sponges #D-3, 60 µm pore size are suitable (Rippey Corp, Kanebo). Similarly, PVA sponges are commercially available from Ivalon Inc. (San Diego, Calif.) and Hydrofera (Cleveland, Ohio). PVA sponges are water-insoluble foams formed by the reaction of aerated Poly(vinyl alcohol) solution with formaldehyde vapor as the crosslinker. The hydroxyl groups on the PVA covalently crosslink with the aldehyde groups to form the polymer network. The foams are flexible and elastic when wetted and semi-rigid when dried.

The filaments used to form the yarn or mesh internal scaffold are formed of any suitable biocompatible, substantially non-degradable material. Materials useful in forming yarns or woven meshes include any biocompatible polymers that are able to be formed into fibres such as, for example, acrylic, polyester, polyethylene, polypropylene, polyacrylonitrile, polyethylene terephthalate, nylon, polyamides, polyurethanes, polybutester, or natural fibres such as cotton, silk, chitin or carbon. Any suitable thermoplastic polymer, thermoplastic elastomer, or other synthetic or natural material with fibre-forming properties may be inserted into a pre-fabricated hollow fibre membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and have a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation or NaOH or KOH etching) to enhance cellular adhesion to the filaments.

In one embodiment, the filaments, preferably organized in a non-random unidirectional orientation, are twisted in bundles to form yarns of varying thickness and void volume. Void volume is defined as the spaces existing between filaments. The void volume in the yarn should vary between 20-95%, but is preferably between 50-95%. The preferred void space between the filaments is between 20-200 µm, sufficient to allow the scaffold to be seeded with cells along the length of the yarn, and to allow the cells to attach to the filaments. The preferred diameter of the filaments comprising the yarn is between 5-100 µm. These filaments should have sufficient mechanical strength to allow twisting into a bundle to comprise a yarn. The filament cross-sectional shape can vary, with circular, rectangular, elliptical, triangular, and star-shaped cross-section being preferred.

In another embodiment, the filaments or yarns are woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

Examples of suitable monofilaments for use in the present invention are found in U.S. Pat. No. 6,627,422. One example is a PET yarn which is woven into a braid. This PET braid was constructed from a 34 strand, 44 denier multifilament yarn woven onto a 760 µm O.D. mandrel with a 16 carrier braider at a pick count of 20 picks per inch (ppI). The PET yarn may also be used in non-woven strands. Another example is nylon monofilaments woven into a braid. This nylon braid was constructed from a 13 strand, 40 denier multifilament yarn woven onto a 760 µm O.D. mandrel with a 16 carrier braider at a pick count of 18 ppI. A further example includes stainless steel multifilaments woven into a braid. This stainless steel braid was constructed from a ribbon woven onto a 900 µm O.D. mandrel with a 16 carrier braider at a pick count of 90 ppi. The tensile strength of these PET, nylon, and stainless steel braids was 2.7, 2.4, and 3.6 kg force at break, respectively.

In one embodiment, a tubular braid is constructed. In an additional embodiment, the braid is inserted into a hollow fibre membrane. In a further embodiment, cells are seeded onto the hollow fibre membrane. In an additional embodiment, the cells are allowed to infiltrate the wall of the mesh tube to maximize the surface area available for cell attachment. In this embodiment, the braid serves both as a cell scaffold matrix and as an inner support for the device. The increase in tensile strength for the braid-supported device is significantly higher than in alternative approaches.

Many different cell types may be encapsulated in the devices according to the present invention. These include well-known, publicly available immortalized cell lines, spontaneously immortalised cell lines as well as dividing primary cell cultures. As cell lines in some embodiments are to be transfected or transduced, clones have to be selected, expanded and cell banked, it is preferable that the cells or cell lines are capable of undergoing a significant number of divisions.

Cell lines with long term propagation potential may be created from a wide variety of cells, including progenitor and/or precursor cells. Also suitable are stem cells including pluripotent and multipotent stem cells, embryonal stem cells, neural stem cells, hematopoletic stem cells.

Examples of cell lines include Chinese hamster ovary cells (CHO); baby hamster kidney cells (BHK); mouse fibroblast-3T3 cells; African green monkey cell lines (including COS-1, COS-7, BSC-1, BSC-40, BMT-10 and Vero); rat adrenal pheochromocytoma (PC12 and PC12A); AT3, rat glial tumor (C6); growth factor expanded stem cells; EGF-responsive neurospheres; bFGF-responsive neural progenitor stem cells derived from the CNS of mammals [Richards et al., PNAS 89: 8591-8595 (1992); Ray et al., PNAS 90: 3602-3606 (1993)]; primary fibroblasts; Schwann cells; astrocytes; β-TC cells; Hep-G2 cells; oligodendrocytes and their precursors; mouse myoblast cells-C2C12; human glial-derived cells-Hs683; human glial-derived cells-A172; porcine glioblasts; chondroblasts isolated from human long bone; rabbit corneal-derived cells (SIRC), and CAC cells.

The invention also contemplates encapsulation of two or more separately transfected cells or cell lines in the same device, each cell line secreting at least one of the desired molecules. Alternatively, separate devices producing each molecule separately may be implanted.

The choice of cell depends upon the intended application. The cells may naturally produce the desired biologically active molecule or may be genetically engineered to do so.

In a preferred embodiment, the cells are of human origin in order to reduce the risk of immune reaction in a human recipient. Even though the cells are encapsulated behind a semipermeable membrane, a non-human cell line inherently produces non-human proteins and metabolites, which—although secreted at a low level—may trigger an immune response in a human host. In the case of implantation into non-human mammals it is preferable that the cells are of the same species as the mammal into which the capsules are to be implanted.

In the broadest aspect this includes any human cell culture or cell line, whether polyclonal or monoclonal. Monoclonal cell lines are more preferable, as they can be better characterised.

Human cell lines may have been immortalised by insertion of a heterologous immortalisation gene, they may be spontaneously immortal, or they may be growth factor expanded primary cells or stem cells.

Preferably, the cell line is a contact inhibited cell line or a cell line, that can differentiate inside the capsule, e.g. a stem cell. By a contact inhibited cell line is intended a cell line which when grown in 2-D cultures grows to confluency and then substantially stops dividing. This does not exclude the possibility that a limited number of cells escape the 2D layer. Contact inhibited cells may also be grown in 3D, e.g. inside a capsule. Also inside the capsules, the cells grow to confluency and then significantly slow down proliferation rate or completely stop dividing.

A particularly preferred type of cells include epithelial cells which are by their nature contact inhibited and which form stable monolayers in culture. Even more preferred are retinal pigment epithelial cells (RPE cells). The source of RPE cells is by primary cell isolation from the mammalian retina. Protocols for harvesting RPE cells are well-defined (Li and Turner, 1988, Exp. Eye Res. 47:911-917; Lopez et al., 1989, invest. Opthalmol. Vis. Sci. 30:586-588) and considered a routine methodology. In most of the published reports of RPE cell cotransplantation, cells are derived from the rat (Li and Turner, 1988; Lopez et al., 1989). According to the present invention RPE cells are derived from humans. In addition to isolated primary RPE cells, cultured human RPE cell lines may be used in the practice of the invention.

All normal diploid vertebrate cells have a limited capacity to proliferate, a phenomenon that has come to be known as the Hayflick limit or replicative senescence. In human fibroblasts, this limit occurs after 50-80 population doublings, after which the cells remain in a viable but non-dividing senescent state for many months. This contrasts to the behavior of most cancer cells, which have escaped from the controls limiting their proliferative capacity and are effectively immortal.

It is preferable that the cells are capable of undergoing a certain number of cell divisions so they can be genetically modified and expanded to produce enough cells for encapsulated cell therapy or transplantation therapy. Accordingly a preferred cell line is capable of undergoing at least 50 doublings, more preferably at least 60 doublings, more preferably at least 70 doublings, more preferably at least 80 doublings, more preferably at least 90 doublings, such as approximately 100 doublings.

For encapsulation, the cells are preferably able to survive and maintain a secretion of a therapeutic molecule at the low oxygen tension levels of the human body, e.g. within the CNS. Preferably the cell line of the invention is capable of surviving at an oxygen tension below 5%, more preferably below 2%, more preferably below 1%. 1% oxygen tension corresponds to the oxygen level in the brain.

A cell line for an encapsulated cell biodelivery should have as many of the following characteristics as possible: (1) The cells should be hardy under stringent conditions (the encapsulated cells should be functional in the vascular and avascular tissue cavities such as in the central nervous system intraparenchymally or within the ventricular or intrathecal fluid spaces or the eye, especially in the intra-ocular environment). (2) The cells should be able to be genetically modified to express a therapeutic molecule. (3) The cells should be able to go through a relatively high number of divisions and have a relatively long life span (the cells should produce sufficient progenies to be banked, characterised, engineered, safety tested and clinical lot manufactured). (4) The cells should be of human origin (which increases compatibility between the encapsulated cells and the host). (5) The cells should exhibit greater than 80% viability for a period of more than one month in vivo in the device (which ensures long-term delivery). (6) The encapsulated cells should deliver an efficacious quantity of a therapeutic molecule (which ensures effectiveness of the treatment). (7) When encapsulated, the cells should not cause a significant host immune reaction (which ensures the longevity of the graft). (8) The cells should be non-tumourigenic (to provide added safety to the host, in case of device leakage).

In a screening and characterisation of several cell lines it has been found that the ARPE-19 cell line (Dunn et al., 62 Exp. Eye Res. 155-69 (1996), Dunn et al., 39 Invest. Opthalmol. Vis. Sci. 2744-9 (1998), Flnnemann et al., 94 Proc. Natl. Acad. Sci. USA 12932-7 (1997), Handa et al., 66 Exp. Eye. 411-9 (1998), Holtkamp et al., 112 Clin. Exp. Immunol. 34-43 (1998), Maidji et al., 70 J. Virol. 8402-10 (1996)) has all of the characteristics of a successful platform cell for an encapsulated cell-based delivery system (U.S. Pat. No. 6,361, 771, Tao et al). The ARPE-19 cell line was superior to the other cell lines tested.

The ARPE-19 cell line is available from the American Type Culture Collection (ATCC Number CRL-2302). The ARPE-19 cell line is derived from cultures of normal retinal pigmented epithelial (RPE) cells and express the retinal pigmentary epithelial cell-specific markers CRALBP and RPE-65. ARPE-19 cells form stable monolayers, which exhibit morphological and functional polarity. ARPE-19 cells may be cultured in Complete Growth Medium, the serum-containing medium recommended by the cell depositor. Complete Growth Medium is either a 1:1 mixture of Dulbecco's modified Eagle's medium and Ham's F12 medium with 3 mM L-glutamine, 90%; foetal bovine serum, 10% or a 1:1 mixture of Dulbecco's modified Eagle's medium and Ham's F12 medium with HEPES buffer containing 10% fetal bovine serum, 56 mM final concentration sodium bicarbonate and 2 mM L-glutamine. The cells are preferably incubated at 37° C. In 5% $CO_2$. The cells are typically plated and grown in Falcon tissue culture treated 6 or 12-well plates or T25 or T75 flasks. For subculturing, medium is removed, and the ARPE-19 cells are preferably rinsed with 0.05% trypsin, 0.02% EDTA solution, and the trypsin is removed. One to two ml of additional trypsin solution is added. The culture is incubated at room temperature (or at 37° C.) until the ARPE-19 cells detach. A subcultivation ratio of 1:3 to 1:5 is recommended.

In another embodiment the cell line is selected from the group consisting of: human immortalised fibroblast cell lines, human immortalised mesencymal stem cell lines, human immortalised astrocyte cell lines, human immortalised mesencephalic cell lines, and human immortalised endothelial cell lines, preferably immortalised with SV40T, vmyc, or the catalytic subunit of telomerase (TERT).

Another type of preferred human cells according to the invention are immortalised human astrocyte cell lines. The method for generating an immortalised human astrocyte cell lines has previously been described (Price T N, Burke J F, Mayne L V. A novel human astrocyte cell line (A735) with astrocyte-specific neurotransmitter function. In Vitro Cell Dev Blol Anim. 1999 May; 35(5):279-88.). This protocol may be used to generate astrocyte cell lines.

Methods for controlling cell distribution within an encapsulation device have also been discussed. See, e.g., U.S. Pat. No. 5,795,790, herein incorporated by reference. The cells are exposed to a treatment that inhibits cell proliferation, promotes cell differentiation, or affects cell attachment to a growth surface within the bioartificial organ. Such treatments include the steps of (1) genetically manipulating cells, (2) exposing the cells to a proliferation-inhibiting compound or a differentiation-inducing compound or removing the cells from exposure to a proliferation-stimulating compound or a differentiation-inhibiting compound; exposing the cells to irradiation, and (3) modifying a growth surface of the encapsulation device with extracellular matrix molecules, molecules affecting cell proliferation or adhesion, or an inert scaffold, or a combination thereof. These treatments may be used in combination. In a preferred treatment, cells are exposed to and then removed from exposure to a proliferation-stimulating and differentiation inhibiting compound prior to encapsulation of the cells in the semipermeable biocompatible membrane. Upon in vivo implantation of the encapsulation device in a host, cellular proliferation is inhibited and cellular differentiation is promoted.

Genetic Engineering of Cells for Encapsulation

Cells can be genetically engineered to overexpress a therapeutic molecule. The terms "genetic modification" and "genetic engineering" refer to the stable or transient alteration of the genotype of a cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

Any useful genetic modification of the cells is within the scope of the invention. For example, cells may be modified to produce or increase production of a biologically active substance such as a neurotransmitter or growth factor or the like. The genetic modification can be performed either by infection with viral vectors (retrovirus, modified herpes viral, herpes-viral, adenovirus, adeno-associated virus, and the like) or transfection using methods known in the art (lipofection, calcium phosphate transfection, DEAE-dextran, electroporation, and the like) (see, Maniatis et al., in Molecular Cloning: A Laboratory Manual (Cold Spring Harbor Laboratory, N.Y., 1982)). For example, the chimeric gene constructs can contain viral, for example retroviral long terminal repeat (LTR), simian virus 40 (SV40), cytomegalovirus (CMV); or mammalian cell-specific promoters. In addition, the vectors can include a drug selection marker, such as the E. coli aminoglycoside phosphotransferase gene, which when co-infected with the test gene, confers resistance to geneticin (G418), a protein synthesis inhibitor.

Cells can be genetically modified using transfection with expression vectors. An "expression vector" is a nucleic acid either integrated in the genome or present in the cytoplasm, and capable of permitting the expression of the polypeptide, protein or viral vector. In one protocol, vector DNA containing the genes are diluted in 0.1×TE (1 mM Tris pH 8.0, 0.1 mM EDTA) to a concentration of 40 μg/ml. 22 μl of the DNA is added to 250 μl of 2×HBS (280 mM NaCl, 10 mM KCl, 1.5 mM $Na_2HPO_4$, 12 mM dextrose, 50 mM HEPES) in a disposable, sterile 5 ml plastic tube. 31 μl of 2 M $CaCl_2$ is added slowly and the mixture is incubated for 30 minutes (min) at room temperature. During this 30 min incubation, the cells are centrifuged at 800 g for 5 min at 4° C. The cells are re-suspended in 20 volumes of ice-cold PBS and divided into aliquots of $1 \times 10^7$ cells, which are again centrifuged. Each aliquot of cells is resuspended in 1 ml of the DNA-$CaCl_2$ suspension, and incubated for 20 min at room temperature. The cells are then diluted in growth medium and incubated for 6-24 hr at 37° C. in 5%-7% $CO_2$. The cells are again centrifuged, washed in PBS and returned to 10 ml of growth medium for 48 hr.

Suitable vehicles for direct DNA, plasmid polynucleotide, or recombinant vector administration include, without limitation, saline, or sucrose, protamine, polybrene, polylysine, polycations, proteins, calcium phosphate, or spermidine. See e.g, WO 94/01139.

Cells can also be genetically modified using calcium phosphate transfection techniques. For standard calcium phosphate transfection, the cells are mechanically dissociated into a single cell suspension and plated on tissue culture-treated dishes at 50% confluence (50,000-75,000 cells/$cm^2$) and allowed to attach overnight. In one protocol, the modified calcium phosphate transfection procedure is performed as follows: DNA (15-25 μg) in sterile TE buffer (10 mM Tris, 0.25 mM EDTA, pH 7.5) diluted to 440 μl with TE, and 60 μl of 2 M $CaCl_2$ (pH to 5.8 with 1M HEPES buffer) is added to the DNA/TE buffer. A total of 500 μl of 2×HeBS (HEPES-Buffered saline; 275 mM NaCl, 10 mM KCl, 1.4 mM $Na_2HPO_4$, mM dextrose, 40 mM HEPES buffer powder, pH 6.92) is added dropwise to this mix. The mixture is allowed to stand at room temperature for 20 min. The cells are washed briefly with 1×HeBS and 1 ml of the calcium phosphate precipitated DNA solution is added to each plate, and the cells are incubated at 37° C. for 20 min. Following this incubation, 10 ml of "Complete Medium" is added to the cells, and the plates are placed in an incubator (37° C., 9.5% $CO_2$) for an additional 3-6 hours. The DNA and the medium are removed by aspiration at the end of the incubation period. The cells are washed, fresh medium is added and then cells are returned to the incubator.

Alternatively, the calcium phosphate co-precipitation technique can be used, as described in WO 93/06222.

Moreover, cells can be genetically engineered to produce a desired secreted factor. The desired secreted factor can be encoded by either a synthetic or recombinant polynucleotide. The term "recombinant" refers to the molecular biological technology for combining polynucleotides to produce useful biological products, and to the polynucleotides and peptides produced by this technology. The polynucleotide can be a recombinant construct (such as a vector or plasmid) which contains the polynucleotide encoding the desired secreted factor under the operative control of polynucleotides encoding regulatory elements such as promoters, termination signals, and the like. "Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence which is transcribed and translated into a polypeptide. Two coding polynucleotides are "operably linked" if the linkage results in a continuously translatable sequence without alteration or interruption of the triplet reading frame. A polynucleotide is operably linked to a gene expression element if the linkage results in the proper function of that gene expression element to result in expression of the desired secreted factor. "Transformation" is the insertion of an exogenous polynucleotide (i.e., a "transgene") into a host cell. The exogenous polynucleotide is integrated within the host genome. A polynucleotide is "capable of expressing" a desired secreted factor if it contains nucleotide sequences which contain transcriptional and translational regulatory information and such sequences are "operably linked" to polynucleotide which encode the desired secreted factor. A polynucleotide that encodes a peptide coding region can be then amplified, for example, by preparation in a bacterial vector, according to conventional methods, for example, described in the standard work Sambrook et al., Molecular Cloning: A Laboratory Manual (Cold Spring Harbor Press 1989). Expression vehicles include plasmids or other vectors.

The polynucleotide encoding the desired secreted factor can be prepared by chemical synthesis methods or by recombinant techniques. The polypeptides can be prepared conventionally by chemical synthesis techniques, such as described by Merrifield, 85 J. Amer. Chem. Soc. 2149-2154 (1963) (see, Stemmer et al, 164 Gene 49 (1995)). Synthetic genes, the in vitro or in vivo transcription and translation of which will result in the production of the desired secreted factor protein can be constructed by techniques well known in the art (see Brown et al., 68 Methods in Enzymology 109-151 (1979)). The coding polynucleotide can be generated using conventional DNA synthesizing apparatus such as the Applied Biosystems Model 380A or 380B DNA synthesizers (commercially available from Applied Biosystems, inc., 850 Lincoln Center Drive, Foster City, Calif., USA).

Polynucleotide gene expression elements useful for the expression of cDNA encoding desired secreted factor include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Recipient cells capable of expressing the desired secreted factor are then transfected. The transfected recipient cells are cultured under conditions that permit expression of the desired secreted factor, which is recovered from the culture. Cells can be used in connection with poxvirus vectors, such as vaccinia or swinepox. Suitable non-pathogenic viruses which can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething & Sambrook, 293 Nature 620-625 (1981)). Another preferred system includes the baculovirus expression system and vectors.

The polynucleotide encoding the desired secreted factor can be used in a variety of ways. For example, a polynucleotide can express the desired secreted factor peptide in vitro in a host cell culture. The expressed desired secreted factor, after suitable purification, can then be incorporated into a pharmaceutical reagent or vaccine (described below).

The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are "neurological agents", a term which encompasses any biologically or pharmaceutically active substance that may prove potentially useful for the proliferation, differentiation or functioning of CNS or eye cells or treatment of neurological or opthalmological disease or disorder. For example, the term may encompass certain neurotransmitters, neurotransmitter receptors, growth factors, growth factor receptors, and the like, as well as enzymes used in the synthesis of these agents.

When the genetic modification is for the production of a biological agent, the substance can be one that is useful for the treatment of a given disorder such as a CNS disorder. Cells can be genetically modified to express a biologically active agent, such as growth factors, growth factor receptors, neurotransmitters, neurotransmitter synthesizing genes, neuropeptides, and chromaffin granule amine transporter. For example, it may be desired to genetically modify cells so they secrete a proliferation-inducing growth factor or a differentiation-inducing growth factor.

The biological agent can be basic fibroblast growth factor (bFGF), acid fibroblast growth factor, epidermal growth factor, transforming growth factor α, transforming growth factor β, nerve growth factor, insulin like growth factor, platelet derived growth factor, glia cell line-derived neurotrophic factor, neurturin, persephin, Neublastin (Artemin), brain derived neurotrophic factor, ciliary neurotrophic factor, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor, or other agents expected to have therapeutically useful effects on potential target tissues. Examples of biological agents include trophic factors such as glial-derived neurotrophic factor (GDNF); regulators of intracellular pathways associated with growth factor activity such as staurosporine, CGP-4 1251, and the like; hormones; various proteins and polypeptides such as interleukins; heparin-like molecules; and a variety of other molecules that have an effect on radial glial cells or CNS neural stem cell.

Mammalian cells that secrete IL-2 can be created by transfection with the plasmid vector pBCMG-hygro-hIL-2 (Roux et al., 159 J. Cell. Physiol. 101-113 (1994)), an episomal expression vector containing the human IL-2 cDNA sequence under the transcriptional control of a cytomegalovirus (CMV) promoter including a rabbit β-globin intron, followed by a poly(A) sequence, and a hygromycin-resistant gene for selection. To introduce an expression vector encoding the hIL-2 protein into the mammalian cell line, the calcium phosphate precipitation technique can be used. The pPCHIL plasmid (pBCMG-hIL-2) contains the hIL-2 cDNA sequence followed by the Hygromycin B resistance gene for selection. Cells which have stably integrated foreign DNA into their genome are selected in presence of Hygromycin B in the medium.

Mammalian cells that secrete IL-10 can be created. Interleukin-10 (IL-10), produced by the Th, subset of $CD_4$ cells, suppresses cytokine production by the $Th_1$, subset of $CD4^+$ helper T-lymphocytes. IL-10 also inhibits the production of numerous pro-inflammatory cytokines by monocytes. IL-10 expression has been detected in human malignant gliomas and at higher levels in malignant vs. low grade tumors. This has led to the hypothesis that endogenous IL-10 functions to suppress anti-glioma immunity within brain. Despite the potentially immunosuppressive and anti-inflammatory actions of endogenous IL-10, evidence is mounting that transgenic IL-10 produced at high levels by engineered tumor cells can inhibit growth of systemic tumors by either stimulating anti-tumor immunity or inhibiting tumor-associated angiogenesis. IL-10-producing mammalian cells can be created by transfection with the plasmid pBMGneo. IL-10 in the presence of lipofectamine (GiBCO) using a procedure similar to that of Kundu et al., 88 J. Natl Cancer inst. 536-41 (1996).

Mammalian cells that secrete FGF can be created. Fibroblast growth factor (FGF) is an endothelial cell mitogen that can be neuroprotective for other cell types within the central nervous system. The mammalian cell line can be genetically altered to express a chimeric human FGF-1 gene consisting of the hst/KS3 signal sequence of FGF-4 fused in-frame to FGF-1 (sp-hst/KS3:FGF-1) (Forough et al., 268 J. Biol. Chem. 2960-8 (1993)).

Mammalian cells can be engineered to produce various neurotransmitters or their receptors such as serotonin, L-dopa, dopamine, norepinephrine, epinephrine, tachykinin, substance P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptldes, which may prove useful in the treatment of CNS disorders, include substance-P, neuropeptide-Y, enkephalin, vasopressin, VIP, glucagon, bombesin, CCK, somatostatin, calcitonin gene-related peptide, and the like.

Alternatively, mammalian cells can be constructed to produce retroviral gene transfer vectors using the methods of U.S. Pat. No. 5,614,404, describing recombinant viral vectors which coexpress heterologous polypeptides capable of assembling into defective nonself-propagating viral particles. Viruses useful as gene transfer vectors include retrovirus, which are the vectors most commonly used in human clinical trials. To generate a gene therapy vector, the gene of interest is cloned into a replication-defective retroviral plasmid which contains two long terminal repeats (LTR), a primer binding site, a packaging signal, and a polypurine tract essential to reverse transcription and the integration functions of retrovirus after infection. To produce viral vector, the plasmid form of a vector is transfected into a packaging cell line which produces Gag, Pol and Env of the retroviral structural proteins required for particle assembly. A producer cell line is usually generated using a selective marker, often a G418 resistant gene carried by the retroviral vector. The resulting cell line can be encapsulated, as described in WO 97/44065, which describes biocompatible capsules containing living packaging cells that secrete a viral vector for infection of a target cell, and methods of delivery for an advantageous infectivity of the target cells.

The effects of the biological agents on cells of the CNS or eye in the recipient host can be identified in vitro based upon significant differences between model cell cultures for central nervous system cells (such as rat pheochromocytoma PC12 cells, cultured primary central nervous neurons, etc.); or eye cells (such as the IO/LD7/4 cell line, ARPE-19 cells, cultured retinal pigment epithelial cells, etc.) relative to control cultures with respect to criteria such as the ratios of expressed phenotypes (neurons, glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which synthesize these molecules. Also, the cellular detection of transcripts of the desired secreted factor in vivo can be demonstrated by immunochemistry or by other immunological methods.

Therapeutic Usefulness of Polymer Encapsulated Cell Delivery of Growth Factors

The central nervous system is site that is subject to chronic degeneration. Growth factors are known to have a tremendous therapeutic potential for treating neuro-degenerative disorders. For example, polymer-encapsulated xenogeneic cells that have been genetically engineered to secrete growth factors can protect against lesion-induced cell loss in the central nervous system in rats (Winn et al., 91 Proc. Natl. Acad. Sci. USA 2324-8 (1994)), primates (Emerich et al., 349 J. Comp.

Neurol. 148-64 (1994)), and aged primates (Kordower et al., 91 Proc. Natl. Acad. Sci. USA 10898-902 (1994)). Therapeutic effects have been produced with polymer-encapsulated cell devices directly delivering various growth factors to a range of target sites in the central nervous system with no evidence of adverse effects (Emerich et al., 130 Exp. Neurol. 141-50 (1994), Emerich et al, 736 Brain Res. 99-110 (1996), Emerich et al., 349 J. Comp. Neurol. 148-64 (1994), Hoffman et al., 122 Exp. Neurol. 100-6 (1993), Kordower et al., 72 Neuroscience 63-77 (1996), Kordower et al., 91 Proc. Natl. Acad. Sci. USA 10898-902 (1994), Winn et al., 91 Proc. Natl. Acad. Sci. USA 2324-8 (1994)). The safety of polymer-encapsulated cell delivery of growth factors is supported by studies that found no adverse effects in animals receiving growth factors delivered to the brain for up to one year (Lindner et al., 5 Cell Transplant. 205-23 (1996), Winn et al., 140 Exp. Neurol. 126-38 (1996)). These studies found no adverse effects even in tests of learned behaviors, which are extremely sensitive to neurotoxicity.

Materials and dimensions may in one specific embodiment be selected as follows:

Example 1

Manufacture of Capsule and Loading of Cells

Capsules

Devices are fabricated from polysulphone (PS), or polyether sulfone (PES) or an equivalent polymer hollow fiber membrane with an outside diameter of 800-1000 μm and a wall thickness of approximately 100 μm. A porous scaffolding material consisting of polyvinyl alcohol (PVA) inserted into the membrane fiber cavity ensures proper cell distribution and attachment of the cell line. Finally, a tether fabricated from polyurethane (PU) or an equivalent material fixed to the device end provides a means for capsule retrieval post-implantation.

Capsules used for pre-clinical testing (in rats) are approximately 5 mm long. Capsules contemplated for implantation into human brains are 5-100 mm long.

Figure 8:
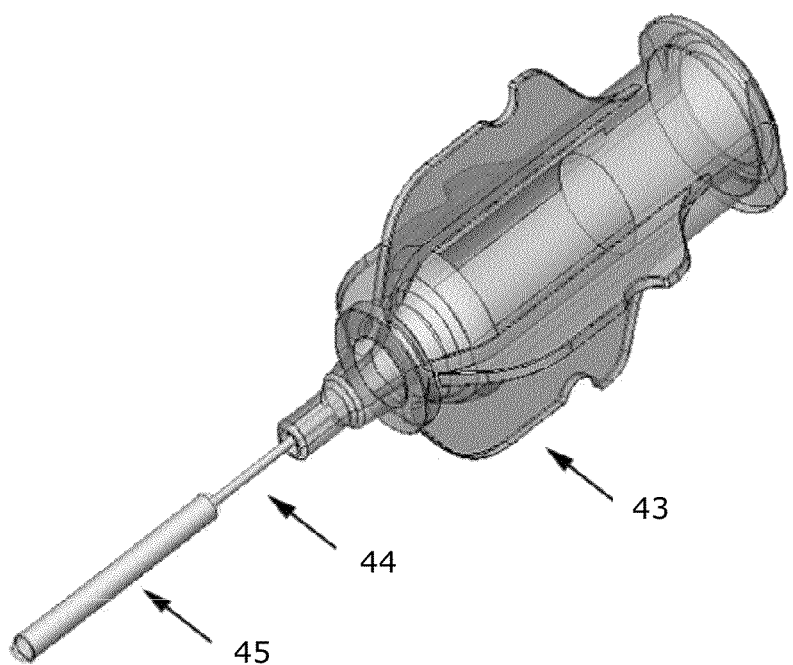
FIG. 8 shows an encapsulation device mounted on the hub 43 by the load tube 44 prior to cell loading. Cells in suspension are injected from a syringe through the load tube by attachment of the hub to the syringe. After cell loading, the load tube is retracted from the capsule and the resulting opening is sealed with glue. The membrane is indicated by numeral 45.

Cellular loading occurs through a hub segment and port attached to the hollow fibre device at the end distal to the tether (FIG. 8). Cells prepared as a single-cell suspension are infused into the port, the hub segment is retrieved and the infusion hole is sealed with glue. For each mm length of the devices, approximately 10,000 cells are loaded (ARPE-19 cells). The ARPE-19 cell line is available from the American Type Culture Collection (ATCC Number CRL-2302). The devices are maintained in media until use.

Capsules for implantation into rat brains were made with the following materials:

Membrane: Polysulphone hollow fiber membrane (PS90/700 from Mlnntech Corp, Minneapolis, Minn., USA), with a 90 kDA molecular weight cutoff. Dimensions: 700 μm+/−50 μm inner diameter, 100 μm+/−20 μm wall. The hollow fibre was cut to lengths of approximately 5 mm.

Foam: PVA foam, product no. 160 LD from Hydrofera Inc, Cleveland, Ohio, USA. The PVA foam was cut to fit the inner diameter of the hollow fiber.

Load tube: Perfluoroalkoxy copolymer, 0.0037"+/−0.0005" ID; 0.005"+/−0.001" wall. From Zeus industrial Products, Orangeburg, S.C., USA. The load tube is glued to the hollow fibre in one end and to the hub in the other end.

Hub: Product no P/N 02030200 Rev 1, from Abtec, Bristol, Pa., USA.

Glue for gluing load tube to hub: Dymax 201-CTH from Dlatom, Hvidovre, Denmark

Glue for hollow fibre: Dymax 1181-M from Dlatom, Hvidovre, Denmark.

Capsules were assembled in a controlled environment.

Example 2

Manufacture of Tether, Stiffener, and Handle

Tether:
Material: Polyurethane (ex. Carbothane from Noveon), or other flexible polymer tubing.
Length: 150+/−5 mm
Outer diameter: 1+/−0.125 mm
Inner diameter: 0.25+/−0.05 mm
Reduced diameter: 0.50+/−0.05 mm
Reduced diameter length: 1.5+/−0.1 mm
Stiffener:
Materials: 0.042"×0.032" 316 series Stainless Steel Welded and Drawn Tubing
0.032"×0.020" 316 series Stainless Steel Welded and Drawn Tubing
0.020"×0.010" 316 series Stainless Steel Welded and Drawn Tubing
0.009" 316 series Stainless Steel Wire
... or other solid material suitable for small-dimension machining (ex. carbon).
Length: Steel wire cut to stop immediately before tether/membrane junction.
Manufacturing: Stainless steel tubing cut to specifications by EDM or laser cutting and welded together by laser welding.
Separate Handle:
Material: 0.042"×0.032" 316 series Stainless Steel Welded and Drawn Tubing or other hard flexible material (ex. carbon).
Manufacturing: Cut to specifications by laser or EDM.
Gripping Element:
Material: Silicone or other flexible, biocompatible polymer with high sliding friction at interference fit.
Manufacturing: Gripping elements are cast individually using a custom designed mould.

Example 3

Manufacture and Packaging of the Therapy System

1. The tether and capsule (with hub segment) is joined using UV-curable glue.
2. Stiffener is inserted into a cavity of the tether.
3. The gripping element is mounted on the tether.
4. The system is mounted in a suitable tray and sterilized by e-beam or gas or similar.
5. The capsule is filled with cells as described above and sealed.
6. The proximal end of the stiffener is attached to a seal of the closure of the container by interference fit.
7. The container is filled with a fluid growth/storage medium and sealed by attaching the closure.

Example 4

Device Implantation

1. Preparatory to the insertion of the therapy system into the patient, the therapy system is withdrawn from the container by removing the closure.

2. The system is removed from closure and attached to the separate handle.
3. The device tip is inserted into the guiding cannula by holding the gripping element and the separate handle.
4. The gripping element is removed and the system is further inserted into the cannula.
5. The tip of the system is. positioned at the tip of the cannula. The separate handle facilitates this operation.
6. The insertion site is surgically exposed, and a cannula and the system is inserted into the implantation or treatment site.
7. The cannula is withdrawn while maintaining system location by use of the separate handle.
8. The Stiffener is withdrawn.
9. The Tether is cut to length and fixed at the insertion site, e.g. to the skull.

In accordance with the invention, the medical practitioner can perform all of the above mentioned steps without touching the capsule or other parts of the system which are to be inserted into the treatment site, and the risk of contaminating the inserted parts of the therapy system is therefore reduced.

The invention claimed is:

1. An implantable therapy system for providing a biologically active compound to an individual, said system comprising:
   a. a cylindrical capsule comprising a proximal end, a distal end, and a biocompatible semi-permeable outer membrane encapsulating isolated cells which are capable of secreting a biologically active compound, the membrane allowing passage of said compound;
   b. an elongated tether, said tether being made from flexible tubing and comprising a proximal end, a distal end, and a conduit originating at said distal end; and
   c. an elongated stiffener by which the system can be handled, comprising a first portion and a second portion, wherein:
      the proximal end of said capsule is joined to the distal end of said elongated tether such that said capsule and elongated tether have co-axial orientation;
      said tether comprises a segment that is non-overlapping with said capsule, said segment of said tether having a radial size greater than or equal to the radial size of the proximal end of said capsule;
      said first portion of said stiffener is disposed in, and detachably attached to, said conduit; and
      said second portion of said stiffener extends from the proximal end of said tether and is non-overlapping with said tether.

2. A system according to claim 1, wherein the capsule has a radial size smaller than the radial size of the tether.

3. A system according to claim 1, wherein the stiffener extends coaxially inside the tether.

4. A system according to claim 1, wherein said first portion of said stiffener has a cross-sectional size and shape which matches the cross-sectional size and shape of the conduit of the tether to establish interference fit therein between thereby to detachably attach the stiffener to the tether.

5. A system according to claim 1, wherein said second portion of said stiffener is wider in the cross-sectional direction than said first portion of said stiffener.

6. A system according to claim 1, wherein the stiffener coextends substantially the entire length of the tether including where there is a clearance between the distal end of the stiffener and the capsule.

7. A system according to claim 1, wherein the stiffener is adhesively bonded to the tether.

8. A system according to claim 7, wherein an outer surface of the stiffener comprises a handling means adapted to engage with a separate handle.

9. A system according to claim 1, further comprising a separate handle for attachment to a handling means of the tether or the stiffener.

10. A method of inserting in an individual an implantable therapy system of claim 1, the system being stored in a container with a closure to which the stiffener or the tether is attached,
said method comprising the steps of:
   a. withdrawing the system from the container by removing a closure of the container,
   b. attaching a separate handle to the tether or to the stiffener,
   c. inserting a tip of the system into a cannula by holding a gripping element and the separate handle,
   d. removing the gripping element and further inserting the system into the cannula,
   e. positioning the tip of the system at a tip of the cannula,
   f. inserting the cannula and the system simultaneously into a surgically exposed insertion site of the individual,
   g. withdrawing the cannula while maintaining the location of the system by use of the separate handle, and
   h. detaching and withdrawing the stiffener from the tether.

11. A system according to claim 1, further comprising a gripping element detachably attached to the tether and/or to the stiffener.

12. A system according to claim 11, wherein the gripping element forms a passage with a cross sectional shape and size, the gripping element being changeable between a relaxed state wherein an inner surface of the passage contacts an outer surface of the tether and/or the stiffener to attach the gripping element to the therapy system and a strained state wherein the passage is deflected to release the therapy system from the gripping element.

13. A system according to claim 12, wherein the gripping element is made from a resilient material.

14. A system according to claim 12, wherein the passage forms the shape of a semicircular incision between a first and a second arm segment.

15. A system according to claim 12, contained in a container which prevents contamination of the capsule and wherein the gripping element is dimensioned relative to the container to prevent contact between the system and inner walls of the container.

16. A system according to claim 12, wherein the gripping element may be shifted between the relaxed and the strained state by application of a releasing pressure to an outer surface of the gripping element.

17. A system according to claim 16, wherein the gripping element further comprises a third and a fourth arm segment extending from the passage in different directions to facilitate application of the releasing pressure.

18. A system according to claim 1, contained in a container which prevents contamination of the capsule.

19. A system according to claim 18, further comprising a gripping element and wherein the gripping element is dimensioned relative to the container to prevent contact between the system and inner walls of the container.

20. A system according to claim 18, wherein the container forms an opening being closed by a closure, wherein the therapy system is attached to the closure, preferably via the stiffener.

21. A system according to claim 20, wherein the closure (32) comprises a seal (34) comprising a fixation member (35) made of a resilient material and provided with an opening dimensioned to fit closely around a portion of at least one of the stiffener and the tether.

22. A system according to claim 20, wherein at least one of the tether and the stiffener extend(s) through the closure and forms an exposed portion located outside the container.

23. A system according to claim 22, wherein the exposed portion of the at least one of the tether and the stiffener extending through the closure and forming the exposed portion comprises a handling means adapted to engage with a separate handle.

* * * * *